United States Patent
Boileau et al.

(10) Patent No.: US 9,427,000 B2
(45) Date of Patent: *Aug. 30, 2016

(54) FELINE PROBIOTIC LACTOBACILLI COMPOSITION AND METHODS

(75) Inventors: Thomas William-Maxwell Boileau, Galloway, OH (US); Barry Pius Kiley, Cork (IE); Liam Diarmuid O'Mahony, Cork (IE); John MacSharry, Cork (IE); Gregory Dean Sunvold, Lewisburg, OH (US)

(73) Assignee: Mars, Incorporated, McLean, VA (US)

( * ) Notice: Subject to any disclaimer, the term of this patent is extended or adjusted under 35 U.S.C. 154(b) by 1243 days.

This patent is subject to a terminal disclaimer.

(21) Appl. No.: 11/443,974

(22) Filed: May 31, 2006

(65) Prior Publication Data

US 2006/0270020 A1 Nov. 30, 2006

Related U.S. Application Data

(60) Provisional application No. 60/692,440, filed on Jun. 21, 2005, provisional application No. 60/686,055, filed on May 31, 2005.

(51) Int. Cl.
| | | |
|---|---|---|
| *A23K 1/00* | (2006.01) | |
| *A23K 1/18* | (2006.01) | |
| *A61K 35/747* | (2015.01) | |
| *C12N 1/20* | (2006.01) | |
| *C12R 1/225* | (2006.01) | |

(52) U.S. Cl.
CPC .............. *A23K 1/008* (2013.01); *A23K 1/009* (2013.01); *A23K 1/1853* (2013.01); *A23K 1/1866* (2013.01); *A61K 35/747* (2013.01); *C12N 1/20* (2013.01); *C12R 1/225* (2013.01)

(58) Field of Classification Search
CPC ...................... A23V 2002/00; A23V 2200/10; A23V 2250/206; A23V 2200/3204; A23V 2200/08; A23V 2200/32; A23V 2250/21; A23C 9/1234; A23C 19/054; A61K 35/747; C12Q 1/6837; C12Q 1/689; A23L 1/0345; A23L 1/30; A23L 1/3014; A23Y 2220/37; A23Y 2220/67; C12R 1/225; C12R 1/25; A23K 1/009; A23K 1/1846; A23K 1/008; A23K 1/1853; A23K 1/1866; A23K 1/164; A23K 1/1753; A23K 1/003; C12N 1/20; C12N 15/52

See application file for complete search history.

(56) References Cited

U.S. PATENT DOCUMENTS

| | | |
|---|---|---|
| 571,521 A | 11/1896 | Heberline et al. |
| 1,086,936 A | 2/1914 | Pounder et al. |
| 1,503,094 A | 7/1924 | Cramer |
| 2,473,773 A | 6/1949 | West |
| 2,540,979 A | 2/1951 | Clymer et al. |
| 2,641,548 A | 6/1953 | Heinrich |
| 3,320,130 A | 5/1967 | Henry |
| 3,398,001 A | 8/1968 | Benson |
| 3,429,426 A | 2/1969 | Wolf et al. |
| 3,431,338 A | 3/1969 | Munzel |
| 3,677,898 A | 7/1972 | Mitsugi et al. |
| 3,897,572 A | 7/1975 | Riggs et al. |
| 3,898,132 A | 8/1975 | Heltrick |
| 3,931,885 A | 1/1976 | Nahill et al. |
| 3,957,974 A | 5/1976 | Hata |
| 3,989,822 A | 11/1976 | Whistler |
| 4,248,857 A | 2/1981 | DeNeale et al. |
| 4,295,567 A | 10/1981 | Knudsen et al. |
| 4,314,995 A | 2/1982 | Hata et al. |
| 4,332,790 A | 6/1982 | Sozzi et al. |
| 4,338,346 A | 7/1982 | Brand |
| 4,399,163 A | 8/1983 | Brennan et al. |
| 4,403,623 A | 9/1983 | Mark |
| 4,411,925 A | 10/1983 | Brennan et al. |
| 4,423,029 A | 12/1983 | Rizzi |
| 4,434,231 A | 2/1984 | Jung |
| 4,518,696 A | 5/1985 | Gehrman et al. |
| 4,592,748 A | 6/1986 | Jost |
| 4,647,453 A | 3/1987 | Meisner |
| 4,736,849 A | 4/1988 | Leonard et al. |
| 4,764,389 A | 8/1988 | Labarge |
| 4,767,623 A | 8/1988 | Conway et al. |
| 4,781,939 A | 11/1988 | Martin et al. |
| 4,786,507 A | 11/1988 | Schmidt |
| 4,797,289 A | 1/1989 | Reddy |
| 4,806,368 A | 2/1989 | Reddy |
| 4,808,626 A | 2/1989 | Friedman et al. |
| 4,814,193 A | 3/1989 | Shenouda et al. |
| 4,816,259 A | 3/1989 | Matthews et al. |

(Continued)

FOREIGN PATENT DOCUMENTS

| | | |
|---|---|---|
| AU | 199642145 | 8/1996 |
| AU | 19928098 A1 | 7/1999 |

(Continued)

OTHER PUBLICATIONS

U.S. Appl. No. 11/013,093, filed Dec. 15, 2004, Boileau et al., Patent No. 2005/0158293 A1.

(Continued)

*Primary Examiner* — Debbie K Ware

(74) *Attorney, Agent, or Firm* — Mars, Incorporated; Becca Barnett

(57) ABSTRACT

According to the invention there is provided a strain of lactic acid bacteria of the genus *Lactobacilli* obtainable by isolation from resected and washed feline gastrointestinal tract having a probiotic activity in animals. Methods of use and compositions comprising the *Lactobacilli* of the present invention are also provided.

35 Claims, No Drawings

(56) References Cited

U.S. PATENT DOCUMENTS

| | | |
|---|---|---|
| 4,859,377 A | 8/1989 | Shasha et al. |
| 4,889,238 A | 12/1989 | Batchelor |
| 4,935,247 A | 6/1990 | Marttila et al. |
| 4,937,077 A | 6/1990 | Deetz, III |
| 5,032,399 A | 7/1991 | Gorbach et al. |
| 5,096,717 A | 3/1992 | Wirth et al. |
| 5,132,137 A | 7/1992 | Reimann et al. |
| 5,160,745 A | 11/1992 | DeLuca et al. |
| 5,171,580 A | 12/1992 | Iamartino et al. |
| 5,286,495 A | 2/1994 | Batich et al. |
| 5,292,657 A | 3/1994 | Rutherford |
| 5,322,686 A | 6/1994 | Grahn et al. |
| 5,344,824 A | 9/1994 | Okuma et al. |
| 5,389,389 A | 2/1995 | Beck |
| 5,413,960 A | 5/1995 | Dobrogosz et al. |
| 5,451,400 A | 9/1995 | Stern et al. |
| 5,474,932 A | 12/1995 | Bengmark et al. |
| 5,501,857 A | 3/1996 | Zimmer |
| 5,501,868 A | 3/1996 | Collings |
| 5,516,684 A | 5/1996 | Saito et al. |
| 5,518,733 A | 5/1996 | Lamothe et al. |
| 5,531,988 A | 7/1996 | Paul |
| 5,538,743 A | 7/1996 | Heinemann et al. |
| 5,540,945 A | 7/1996 | Ikushima |
| 5,569,634 A | 10/1996 | Miller et al. |
| 5,578,302 A | 11/1996 | Brassart et al. |
| 5,582,643 A | 12/1996 | Takei et al. |
| 5,603,930 A | 2/1997 | Brassart |
| 5,629,017 A | 5/1997 | Pozzi et al. |
| 5,645,830 A | 7/1997 | Reid |
| 5,726,161 A | 3/1998 | Whistler |
| 5,733,540 A | 3/1998 | Lee |
| 5,756,088 A | 5/1998 | Matsuura et al. |
| 5,766,520 A | 6/1998 | Bronshtein |
| 5,785,990 A | 7/1998 | Langrehr |
| 5,824,779 A | 10/1998 | Koegel et al. |
| 5,849,327 A | 12/1998 | Berliner et al. |
| 5,853,697 A | 12/1998 | Strober et al. |
| 5,854,067 A | 12/1998 | Newgard et al. |
| 5,858,356 A | 1/1999 | Wolf et al. |
| 5,871,794 A | 2/1999 | Brito |
| 5,871,802 A | 2/1999 | Gao |
| 5,894,029 A | 4/1999 | Brown et al. |
| 5,910,447 A | 6/1999 | Lawrence et al. |
| 5,939,117 A | 8/1999 | Chen et al. |
| 5,962,043 A | 10/1999 | Jones |
| 5,976,579 A | 11/1999 | McLean |
| 6,007,808 A | 12/1999 | DeHaen et al. |
| 6,010,725 A | 1/2000 | Meister et al. |
| 6,033,888 A | 3/2000 | Batich et al. |
| 6,042,857 A | 3/2000 | Jones et al. |
| 6,063,414 A | 5/2000 | Jones et al. |
| 6,077,530 A | 6/2000 | Weinstein et al. |
| 6,080,401 A | 6/2000 | Reddy et al. |
| 6,083,520 A | 7/2000 | Toneby |
| 6,117,477 A | 9/2000 | Paluch et al. |
| 6,133,323 A | 10/2000 | Hayek |
| 6,156,355 A | 12/2000 | Shields et al. |
| 6,190,591 B1 | 2/2001 | Van Lengerich |
| 6,214,336 B1 | 4/2001 | Bukowska et al. |
| 6,254,886 B1 | 7/2001 | Fusca et al. |
| 6,309,666 B1 | 10/2001 | Hatano et al. |
| 6,310,090 B1 | 10/2001 | Hayek |
| 6,355,242 B1 | 3/2002 | Allison et al. |
| 6,358,555 B1 | 3/2002 | Takahashi |
| 6,375,956 B1 | 4/2002 | Hermelin et al. |
| 6,394,803 B1 | 5/2002 | Salz et al. |
| 6,406,853 B1 | 6/2002 | Spindler |
| 6,500,463 B1 | 12/2002 | Van Lengerich |
| 6,506,389 B2 | 1/2003 | Leer et al. |
| 6,537,544 B1 | 3/2003 | Johansson et al. |
| 6,562,336 B2 | 5/2003 | De Simone |
| 6,572,854 B1 | 6/2003 | De Simone |
| 6,586,027 B2 | 7/2003 | Axelrod et al. |
| 6,588,180 B2 | 7/2003 | Heath |
| 6,592,863 B2 | 7/2003 | Fuchs et al. |
| 6,596,946 B2 | 7/2003 | Yagi |
| 6,620,440 B1 | 9/2003 | Hsia |
| 6,624,162 B2 | 9/2003 | Uchida et al. |
| 6,681,935 B1 | 1/2004 | Lewis |
| 6,723,358 B1 | 4/2004 | Van Lengerich |
| 6,733,795 B2 | 5/2004 | Piccirilli et al. |
| 6,737,089 B2 | 5/2004 | Wadsworth et al. |
| 6,746,672 B2 | 6/2004 | O'Sullivan |
| 6,767,573 B1 | 7/2004 | Dixon et al. |
| 6,797,266 B2 | 9/2004 | Naidu |
| 6,802,422 B2 | 10/2004 | Kalvelage et al. |
| 6,827,957 B2 | 12/2004 | Paluch et al. |
| 6,835,376 B1 | 12/2004 | Neeser et al. |
| 6,835,397 B2 | 12/2004 | Lee et al. |
| 6,893,662 B2 | 5/2005 | Dittmar et al. |
| 6,905,679 B1 | 6/2005 | Schiffrin et al. |
| 6,932,990 B2 | 8/2005 | Konishi et al. |
| 6,974,594 B2 | 12/2005 | Ko et al. |
| 6,979,675 B2 | 12/2005 | Tidmarsh |
| 6,991,819 B2 | 1/2006 | Pannevis et al. |
| 7,008,648 B2 | 3/2006 | Corley et al. |
| 7,029,669 B1 | 4/2006 | Reniero et al. |
| 7,037,708 B1 | 5/2006 | Runge et al. |
| 7,052,688 B2 | 5/2006 | De Simone |
| 7,081,478 B2 | 7/2006 | Hauptmann et al. |
| 7,097,831 B1 | 8/2006 | Bengs et al. |
| 7,115,297 B2 | 10/2006 | Stillman et al. |
| RE39,436 E | 12/2006 | Spindler et al. |
| 7,179,460 B2 | 2/2007 | Dennin et al. |
| 7,201,923 B1 | 4/2007 | Van Lengerich et al. |
| 7,229,818 B2 | 6/2007 | Porubcan |
| 7,235,276 B2 | 6/2007 | Allen et al. |
| 7,235,395 B2 | 6/2007 | Stadler et al. |
| 7,427,398 B2 | 9/2008 | Baillon et al. |
| 7,498,162 B2 | 3/2009 | Germond et al. |
| 7,544,497 B2 | 6/2009 | Sinclair et al. |
| 7,547,527 B2 | 6/2009 | Baur et al. |
| 7,550,285 B2 | 6/2009 | Schiffrin et al. |
| 7,604,809 B2 | 10/2009 | Postaire et al. |
| 7,647,098 B2 | 1/2010 | Prichep |
| 7,666,459 B2 | 2/2010 | Hayek et al. |
| 7,674,808 B2 | 3/2010 | Bueno Calderon et al. |
| 7,687,077 B2 | 3/2010 | Khoo |
| 7,687,085 B2 | 3/2010 | Hayashi et al. |
| 7,700,141 B2 | 4/2010 | Baillon et al. |
| 7,700,315 B2 | 4/2010 | Arigoni et al. |
| 7,771,982 B2 | 8/2010 | Zink et al. |
| 7,785,635 B1 * | 8/2010 | Boileau et al. ............... 424/558 |
| 7,795,227 B2 | 9/2010 | Kriegler et al. |
| 7,816,547 B2 | 10/2010 | Msika et al. |
| 7,833,554 B2 | 11/2010 | Piccirilli et al. |
| 7,838,057 B2 | 11/2010 | Schmidt et al. |
| 7,842,329 B2 | 11/2010 | Saylock et al. |
| 7,897,579 B2 | 3/2011 | Piccirilli et al. |
| 7,906,112 B2 | 3/2011 | Boileau et al. |
| 7,910,144 B2 | 3/2011 | Ballevre et al. |
| 7,935,334 B2 | 5/2011 | Lin |
| 7,960,605 B2 | 6/2011 | Zhao-Wilson |
| 8,030,279 B2 | 10/2011 | Joullie |
| 8,034,601 B2 | 10/2011 | Boileau et al. |
| 8,057,840 B2 | 11/2011 | Harrison et al. |
| 8,092,608 B2 | 1/2012 | Rochat et al. |
| 8,101,170 B2 | 1/2012 | Plail et al. |
| 8,142,810 B2 | 3/2012 | Sunvold et al. |
| 8,263,146 B2 | 9/2012 | Bengtsson-Riveros et al. |
| 8,329,190 B2 | 12/2012 | Vidal et al. |
| 8,349,377 B2 | 1/2013 | Piccirilli et al. |
| 8,394,370 B2 | 3/2013 | Garcia-Rodenas et al. |
| 8,486,389 B2 | 7/2013 | Sidhu et al. |
| 8,524,304 B2 | 9/2013 | Prakash et al. |
| 8,540,980 B2 | 9/2013 | London et al. |
| 8,557,764 B2 | 10/2013 | Newell et al. |
| 8,563,522 B2 | 10/2013 | Pitha et al. |
| 8,663,729 B2 | 3/2014 | Hayek et al. |
| 8,691,303 B2 | 4/2014 | Sunvold et al. |
| 8,722,112 B2 | 5/2014 | Zicker et al. |
| 8,728,559 B2 | 5/2014 | Hayek et al. |
| 8,771,675 B2 | 7/2014 | Zink et al. |

(56) References Cited

U.S. PATENT DOCUMENTS

| | | |
|---|---|---|
| 8,802,158 B2 | 8/2014 | Boileau et al. |
| 8,802,179 B2 | 8/2014 | Miller |
| 8,808,770 B2 | 8/2014 | Henderson et al. |
| 8,865,197 B2 | 10/2014 | Tandler et al. |
| 8,900,569 B2 | 12/2014 | Boileau et al. |
| 8,916,145 B2 | 12/2014 | Mercenier et al. |
| 8,962,007 B2 | 2/2015 | Perez et al. |
| 9,023,810 B2 | 5/2015 | Piccirilli et al. |
| 9,089,576 B2 | 7/2015 | Piccirilli et al. |
| 9,119,843 B2 | 9/2015 | Chen et al. |
| 9,192,177 B2 | 11/2015 | Boileau et al. |
| 2001/0018048 A1 | 8/2001 | Leer et al. |
| 2001/0018071 A1 | 8/2001 | Cochran et al. |
| 2002/0022019 A1 | 2/2002 | Laulund |
| 2002/0035071 A1 | 3/2002 | Pitha et al. |
| 2002/0098235 A1 | 7/2002 | Dittmar et al. |
| 2002/0119237 A1 | 8/2002 | Hevey |
| 2002/0127211 A1 | 9/2002 | Brassart et al. |
| 2003/0049240 A1 | 3/2003 | Ballevre et al. |
| 2003/0060503 A1 | 3/2003 | Hamilton |
| 2003/0092669 A1 | 5/2003 | Chapnick et al. |
| 2003/0104090 A1 | 6/2003 | Levy et al. |
| 2003/0143293 A1 | 7/2003 | Shushunov |
| 2003/0157166 A1 | 8/2003 | Chen et al. |
| 2003/0170217 A1 | 9/2003 | Collins et al. |
| 2003/0170355 A1 | 9/2003 | Glazier et al. |
| 2003/0190309 A1 | 10/2003 | Zink et al. |
| 2003/0190314 A1 | 10/2003 | Campbell et al. |
| 2003/0194423 A1 | 10/2003 | Torney et al. |
| 2004/0001817 A1 | 1/2004 | Giampapa et al. |
| 2004/0047896 A1 | 3/2004 | Malnoe et al. |
| 2004/0161422 A1 | 8/2004 | Ranganathan |
| 2004/0167229 A1 | 8/2004 | Bakker-Arkema et al. |
| 2004/0175389 A1 | 9/2004 | Porubcan |
| 2004/0228933 A1 | 11/2004 | Chapnick |
| 2004/0234579 A1 | 11/2004 | Finke |
| 2004/0253357 A1 | 12/2004 | De Zarate |
| 2005/0074519 A1 | 4/2005 | Bartnick et al. |
| 2005/0079244 A1 | 4/2005 | Giffard et al. |
| 2005/0084479 A1 | 4/2005 | Corthesy-Theulay et al. |
| 2005/0100617 A1 | 5/2005 | Malnoe et al. |
| 2005/0106131 A1 | 5/2005 | Breton et al. |
| 2005/0106133 A1* | 5/2005 | Zink et al. ............... 424/93.45 |
| 2005/0112259 A1 | 5/2005 | Qvyjt |
| 2005/0152884 A1 | 7/2005 | Boileau et al. |
| 2005/0153018 A1 | 7/2005 | Ubbink et al. |
| 2005/0158293 A1 | 7/2005 | Boileau et al. |
| 2005/0158294 A1 | 7/2005 | Boileau et al. |
| 2005/0164978 A1 | 7/2005 | Chapnick et al. |
| 2005/0175598 A1 | 8/2005 | Boileau et al. |
| 2005/0180961 A1 | 8/2005 | Pequet et al. |
| 2005/0208163 A1 | 9/2005 | Brovelli et al. |
| 2005/0249837 A1 | 11/2005 | Massimino et al. |
| 2005/0249841 A1 | 11/2005 | Hayek et al. |
| 2005/0266438 A1 | 12/2005 | Spindler |
| 2005/0281910 A1 | 12/2005 | Schiffrin et al. |
| 2006/0002909 A1 | 1/2006 | Takeda |
| 2006/0008511 A1 | 1/2006 | Lin et al. |
| 2006/0070895 A1 | 4/2006 | Khawaja |
| 2006/0099196 A1 | 5/2006 | Breton et al. |
| 2006/0100162 A1 | 5/2006 | Pitha et al. |
| 2006/0116330 A1 | 6/2006 | Pitha et al. |
| 2006/0147962 A1 | 7/2006 | Jones et al. |
| 2006/0165670 A1 | 7/2006 | Berr et al. |
| 2006/0228448 A1 | 10/2006 | Boileau et al. |
| 2006/0228459 A1 | 10/2006 | Tribelhorn et al. |
| 2006/0263416 A1 | 11/2006 | Brent, Jr. |
| 2007/0009577 A1 | 1/2007 | Mankovitz |
| 2007/0031441 A1 | 2/2007 | Collins et al. |
| 2007/0082107 A1 | 4/2007 | Almutis et al. |
| 2007/0098744 A1 | 5/2007 | Knorr et al. |
| 2007/0116853 A1 | 5/2007 | Krohn et al. |
| 2007/0122531 A1 | 5/2007 | Considini |
| 2007/0123460 A1 | 5/2007 | Chang et al. |
| 2007/0129428 A1 | 6/2007 | Richelle et al. |
| 2007/0149466 A1 | 6/2007 | Milburn et al. |
| 2007/0160589 A1 | 7/2007 | Mattson et al. |
| 2007/0166295 A1 | 7/2007 | Schildgen et al. |
| 2007/0178078 A1 | 8/2007 | Khoo |
| 2007/0190171 A1 | 8/2007 | Yamka et al. |
| 2007/0218164 A1 | 9/2007 | Stojanovic |
| 2007/0231371 A1 | 10/2007 | Pan et al. |
| 2007/0269515 A1 | 11/2007 | Henriksen et al. |
| 2007/0269553 A1 | 11/2007 | Le et al. |
| 2007/0280964 A1 | 12/2007 | Knorr et al. |
| 2007/0286935 A1 | 12/2007 | Grigorov et al. |
| 2008/0044481 A1 | 2/2008 | Harel |
| 2008/0050354 A1 | 2/2008 | Garault et al. |
| 2008/0050355 A1 | 2/2008 | Vaslin |
| 2008/0053490 A1 | 3/2008 | Clark et al. |
| 2008/0107699 A1 | 5/2008 | Spigelman et al. |
| 2008/0145341 A1 | 6/2008 | Myatt et al. |
| 2008/0214479 A1 | 9/2008 | Pitha et al. |
| 2008/0241226 A1 | 10/2008 | Abeln et al. |
| 2008/0260696 A1 | 10/2008 | Massimino et al. |
| 2008/0260866 A1 | 10/2008 | Massimino et al. |
| 2008/0279786 A1 | 11/2008 | Cash |
| 2008/0280274 A1 | 11/2008 | Freisen et al. |
| 2008/0305210 A1 | 12/2008 | Petersen |
| 2008/0311226 A1 | 12/2008 | Yamka et al. |
| 2008/0317905 A1 | 12/2008 | Yamka et al. |
| 2009/0252834 A1 | 10/2009 | Hayek et al. |
| 2009/0263542 A1 | 10/2009 | Lin et al. |
| 2009/0274796 A1 | 11/2009 | Yamka et al. |
| 2009/0324761 A1 | 12/2009 | Khoo et al. |
| 2010/0003369 A1 | 1/2010 | Ter Haar et al. |
| 2010/0112003 A1 | 5/2010 | Collins et al. |
| 2010/0158070 A1 | 6/2010 | Steinboeck et al. |
| 2010/0203225 A1 | 8/2010 | Kerr et al. |
| 2010/0233320 A1 | 9/2010 | Sunvold et al. |
| 2010/0316769 A1 | 12/2010 | Czarnecki-Maulden et al. |
| 2011/0117068 A1 | 5/2011 | Lang et al. |
| 2012/0115798 A1 | 5/2012 | Massimino et al. |
| 2012/0282373 A1 | 11/2012 | Luhadiya et al. |
| 2012/0283197 A1 | 11/2012 | Luhadiya et al. |
| 2013/0183255 A1 | 7/2013 | Saunois et al. |
| 2014/0274920 A1 | 9/2014 | Davenport |
| 2014/0348975 A1 | 11/2014 | Davenport et al. |
| 2014/0348986 A1 | 11/2014 | Beyer et al. |
| 2014/0349002 A1 | 11/2014 | Beyer |
| 2015/0132420 A1 | 5/2015 | Martinez-Serna Villagran et al. |
| 2015/0208679 A1 | 7/2015 | Mir et al. |

FOREIGN PATENT DOCUMENTS

| | | |
|---|---|---|
| CA | 1300538 | 5/1992 |
| CA | 2093287 | 10/1993 |
| CA | 2256256 | 6/2000 |
| CA | 2569249 | 11/2005 |
| DE | 3715070 | 11/1988 |
| DE | 19819475 A1 | 4/1989 |
| DE | 4018392 | 12/1991 |
| DE | 19860375 A1 | 12/1998 |
| DE | 10217970 | 11/2003 |
| EP | 0168112 | 1/1986 |
| EP | 0181170 | 5/1986 |
| EP | 0212746 A2 | 3/1987 |
| EP | 0212747 | 3/1987 |
| EP | 0212747 A2 | 3/1987 |
| EP | 0298605 A1 | 11/1989 |
| EP | 0298605 B1 | 11/1989 |
| EP | 0366621 A1 | 2/1990 |
| EP | 0353581 A2 | 7/1990 |
| EP | 0391416 A1 | 10/1990 |
| EP | 0399819 A2 | 11/1990 |
| EP | 0439315 B1 | 7/1991 |
| EP | 0563934 | 10/1993 |
| EP | 0627173 A1 | 7/1994 |
| EP | 0659769 A2 | 6/1995 |
| EP | 0659769 B1 | 6/1995 |
| EP | 0399819 B1 | 10/1995 |
| EP | 0508701 B1 | 10/1995 |
| EP | 0850569 A1 | 1/1998 |
| EP | 0850569 | 7/1998 |

(56) References Cited

FOREIGN PATENT DOCUMENTS

| | | |
|---|---|---|
| EP | 0862863 B1 | 9/1998 |
| EP | 0956858 A1 | 11/1999 |
| EP | 0956858 B1 | 11/1999 |
| EP | 1010372 A2 | 6/2000 |
| EP | 0850569 B1 | 12/2000 |
| EP | 1312667 A1 | 5/2003 |
| EP | 1547466 | 6/2005 |
| EP | 1637041 | 3/2006 |
| EP | 1806056 | 7/2007 |
| EP | 1806057 | 7/2007 |
| FR | 2663198 | 12/1991 |
| FR | 2668081 A1 | 4/1992 |
| FR | 2615203 A1 | 11/1998 |
| GB | 1190387 | 5/1970 |
| GB | 1595054 | 8/1976 |
| GB | 1503094 | 3/1978 |
| GB | 2241421 A | 4/1991 |
| GB | 2252228 A | 5/1992 |
| GB | 2245492 A | 8/1992 |
| GB | 2311027 A | 9/1997 |
| JP | S59213368 | 12/1984 |
| JP | S6024153 | 2/1985 |
| JP | S6297221 | 5/1987 |
| JP | 62201823 | 9/1987 |
| JP | 03076561 | 4/1991 |
| JP | 94256170 A | 9/1994 |
| JP | 96242763 A | 9/1996 |
| JP | 2000-191519 | 11/2000 |
| JP | 01278781 A | 10/2001 |
| JP | 2001278781 | 10/2001 |
| JP | 2001309753 | 11/2001 |
| JP | 2007117083 | 11/2001 |
| JP | 1995378530 | 8/2003 |
| JP | 2004173675 | 6/2004 |
| JP | 2006055145 | 3/2006 |
| KR | 20020050048 | 6/2002 |
| KR | 20040024774 | 3/2004 |
| RU | 2086248 C | 8/1997 |
| RU | 2123343 C1 | 12/1998 |
| RU | 2388320 | 5/2010 |
| RU | 2407401 | 12/2010 |
| WO | WO 88/08452 A1 | 11/1988 |
| WO | WO 89/05849 A1 | 6/1989 |
| WO | WO 90/01335 A1 | 2/1990 |
| WO | WO 91/17672 A1 | 11/1991 |
| WO | WO 93/02558 A1 | 2/1993 |
| WO | WO 94/04180 A2 | 3/1994 |
| WO | WO 94104180 A3 | 3/1994 |
| WO | WO 94/21284 A1 | 9/1994 |
| WO | 9503809 | 2/1995 |
| WO | WO 95/07090 A1 | 3/1995 |
| WO | WO 95/34292 A2 | 12/1995 |
| WO | WO 96/01612 A1 | 1/1996 |
| WO | WO 96/38159 A1 | 12/1996 |
| WO | WO 97/09448 A1 | 3/1997 |
| WO | WO 97/16198 A1 | 5/1997 |
| WO | WO 97/20577 A1 | 6/1997 |
| WO | WO 98/19968 A1 | 5/1998 |
| WO | WO 98/23727 A1 | 6/1998 |
| WO | WO 98/27967 A1 | 7/1998 |
| WO | WO 98/35014 A2 | 8/1998 |
| WO | WO 98/35014 A3 | 8/1998 |
| WO | WO 98/47374 A1 | 10/1998 |
| WO | WO 98/54982 A1 | 12/1998 |
| WO | WO 99/09839 A1 | 3/1999 |
| WO | WO 99/11245 A1 | 3/1999 |
| WO | WO 99/20745 A1 | 4/1999 |
| WO | WO 99/30576 A1 | 6/1999 |
| WO | WO 99148372 A1 | 9/1999 |
| WO | WO 99/51108 A1 | 10/1999 |
| WO | WO 99/52511 A1 | 10/1999 |
| WO | WO 00/06127 A1 | 2/2000 |
| WO | WO 00/27364 A1 | 5/2000 |
| WO | WO 00/41707 A2 | 7/2000 |
| WO | WO 00/42168 A2 | 7/2000 |
| WO | WO 00/57712 A1 | 10/2000 |
| WO | WO 01/12164 A1 | 2/2001 |
| WO | 01/90311 | 11/2001 |
| WO | WO 01/90311 A2 | 12/2001 |
| WO | WO 01/93011 A3 | 12/2001 |
| WO | WO 02/083879 A2 | 10/2002 |
| WO | WO 03/010297 A1 | 2/2003 |
| WO | WO 03/010298 | 2/2003 |
| WO | WO 03/010298 A1 | 2/2003 |
| WO | WO 03/010299 A1 | 2/2003 |
| WO | WO 03/045356 A1 | 6/2003 |
| WO | 03/075676 | 9/2003 |
| WO | 2004074496 | 9/2004 |
| WO | 2004/098622 A2 * | 11/2004 |
| WO | 2004100670 | 11/2004 |
| WO | WO 2005/060707 A2 | 7/2005 |
| WO | 2005070232 | 8/2005 |
| WO | 2005092116 | 10/2005 |
| WO | 2007060539 | 5/2007 |
| WO | 2007/126990 | 11/2007 |
| WO | 2007137808 | 12/2007 |

OTHER PUBLICATIONS

U.S. Appl. No. 11/012,570, filed Dec. 15, 2004, Boileau et al.
U.S. Appl. No. 11/012,947, filed Dec. 15, 2004, Boileau et al., Patent No. 2005/0175598.
U.S. Appl. No. 11/012,946, filed Dec. 15, 2004, Boileau et al., Patent No. 2005/0152884 A1.
U.S. Appl. No. 11/013,117, filed Dec. 15, 2004 Boileau et al., Patent No. 2005/0158294 A1.
U.S. Appl. No. 11/443,765, filed May 31, 2006, Boileau et al.
Aga, Abstracts, Gastroenterology, vol. 116, No. 4.
Anand et al., "Cytokines and Inflammatory Bowel Disease," Tropical Gastroenterology, 1999, 20 (3), pp. 97-106.
Andus et al., "Imbalance of the Interleukin 1 System in Colonic Mucosa—Association With Intestinal Inflammation and Interleukin 1 Receptor Agonist Genotype 2," Gut, vol. 41, 1997, pp. 651-657, p. 654, col. 2-p. 655, col. 1, fig. 2D.
Arai et al., "Cytokines: Coordinates of Immune and Inflammatory Responses," Aram. Rev. Biochem. 90, 59: 783-836.
Aranda et al., "Analysis of Intestinal Lymphocytes in Mouse Colitis Medicated by Transfer of CD4+, CD45RB high T Cells to SCID Recipients," 1997, The American Assoc. of Immunologists.
Barbara G., et al., A Role for Inflammation in Irritable Bowel Syndrome, Gut, 51, pp. i41-i44.
Binder, Henry J., M.D., "Genes, Bacteria and T Cells: Ingredients for Inflammatory Bowel Disease," Selected Summaries, Gastroenterology, 1998, 115, pp. 1695-1700, vol. 115, No. 6.
Bodmeier R., "Capsule With Controlled Active Ingredient Release Comprises Active Ingredient-Containing Filling, Capsule Shell, Swelling Agent and Water-Insoluble Layer," BODM, May 18, 1999.
Bouhnik et al., "Effects of Bffidobacterium SP Fermented Milk Ingested with or without Inulin on Colonic Bifidobacteria and Enezymatic Activities in Healthy Humans," European Journal of Clinical Nutrition, 1996, 50, pp. 269-273.
Brandtzaeg et al., "Immunopathology of Human Inflammatory Bowel Disease," S .rin • er Seminars in Immuno matholo • , 1997, 18, p. 555-589.
Chadwick et al., "Activation of the Mucosal Immune System in Irritable Bowel Syndrome," Gastroenterology, 2002, 122, pp. 1778-83.
Charteris et al., "Antiobiotic Sysceptibility of Potentially Probiotic Bifidobacterium Isolates From the Human Gastrointestinal Tract," Letters in Applied Microbiology, 1998, vol. 26, pp. 333-337.
Charteris et al., "Development and application of an In Vitro Methodologoy to Determine the Transit Tolerance of Potentially Probiotic Lactobacillus and Bifidobacteriurn Species in the Upper Human Gastrointestinal Tract," Journal of Applied Microbiology, 1998, vol. 84, pp. 759-768.
Charteris et al., "Selective Detection, Enumeration and Identification of Potentially Probiotic Lactobacillus and Bifidobacterium Species in Mixed Bacterial Populations," International Journal of Food Microbiology 35, 1997, pp. 1-27.

(56) References Cited

OTHER PUBLICATIONS

Charteris et al., "Effect of Conjugated Bile Salts on Antibiotic Susceptibility of Bile Salt-Tolerant Lactobacillus and Bifidobacterium Isolates," Journal of Food Protection, vol. 63, No. 10, 2000, pp. 1369-1376.

Chauviere et al., "Adhension of Human Lactobacillus Acidophilus Strain LB to Human Enterocyte-like Caco-2 Cells," Journal of General Microbiology, 1992, vol. 138, pp. 1689-1696.

Chevalier et al., "Detection of Bifidobacterium Species by Enzymatic Methods," Journal of Applied Basteriology, 1990, vol. 68, pp. 619-624

Cicco et al., "Inducible Production of Interluekin-6 by Human Polymorphonuclear Neutrophils: Role of Granulocyte-Macrophage Cology-Stiumulating Factor and Tumor Necrosis Factor-Alpha," 1990, The American Society of Hematology, Blood, vol. 75, No. 10, May 15, 1990, pp. 2049-2052.

Collins et al., "Selection of Probiotic Strains for Human Applications," In. Dairy Journal 8, 1998, 487-490.

Donnelly et al., "Differential Regulation of II-1 Production in Human Monocytes by IFN-y and IL-4," The Journal of Immunology, vol. 145, pp. 569-575, No. 2, Jul. 15, 1990.

Dorland's Pocket Medical Dictionary ($24^{th}$ ed.), W. B. Saunders Co., p. 15, 1989.

Dunne et al., "Probiotics: From Myth to Reality. Demonstration of Functionality in Animal Models of Disease and in Human Clinical Trials.".

Eisai KK, "Sustained-Release Solid Prepn. Of Zero Order Drug Releasing Profile Comprises Granules Obtainable by Coating Inner Core Containing Xanthine Deriv. Etc. with Film of Hardend Oil," EISA, Dec. 22, 1989.

Favier et al., "Fecal B-D-Galactosidase Production and Bifidobacteria Are Decreased in Crohn's Disease," Digestive Diseases and Sciences, vol. 42, No. 4, 4/97, pp. 817-822.

Fergus Shanahan, "The Intestinal Immune System," Physiology of the Gastrointestinal Tract, $3^{rd}$ ed., 1994.

Fishbein, "Biological Effects of Dietary Restriction," Springer, New York, 1991.

Freund Sangyokk, "Capsule Containing Useful Enteric Bacteria-Includes Hydrophobic Layer Non-Fluid At Room Temp Isolating Bacteria From Membrane, to Prevent Moisture Penetration," Derwent Pub. Ltd., FREN, Aug. 5, 1986.

Fujisawa Pharm Co Ltd., "Long-Acting Oral Prepn.—Comprises Rapidly Soluble Inner Layer and Sustained-Release Outer Layer, Both Layers Containing Principal Agent, Which Is Coronary or Peripheral Vasodilator (jpn)," FUJI, Sep. 20, 1991.

Gasche et al., "IL-10 Secretion and Sensitivity in Normal Human Intestine and Inflammatory Bowel Disease," Journal of Clinical Immunology, vol. 20, No. 5, 2000.

Gibson et al., "Dietary Modulation of the Human Gut Microflora Using Prebiotics," Journal of Nutrition, 1998, 80, suppl. 2 S209-S212.

Groux et al., "Regulatory T Cells and Inflammatory Bowel Disease," Viewpoint Immunologoy Today, Oct. 1999.

Hideo Tomomatsu, "Health Effects of Oligosaccharides," 1994, Food Technology 48, pp. 61-65.

Hildesheim et al., "Simultaneous Measurement of Several Cytokines Using Small Volumes of Biospecimens," Cancer Epidemiology, Biomarkers & Prevention, vol. IKI, pp. 1477-1484, Nov. 2002, abstract.

Hommes et al., "Anti- and Proinflammatory Cytokines in the Pathogenesis of Tissue Damage in Crohn's Disease," 2000 Lippincott Williams and Wilkins, pp. 1363-1950.

Iwasaki et al., "Unique Functions of CD11b+, CD8a+ and Double-Negative Peyer's Patch Dendritic Cells," 2001, The American Association of Immunologists.

Kalant et al., "Effect of Diet Restriction on Glucose Metabolism and Insulin Responsiveness and Aging Rats," Mech. Aging Dev., vol. 46, pp. 89-104, 1998.

Kyoto Yakumn KK, "Sustains-Release Formulation Which Floats in Stomach-Comprises Core of Fats and Oils, Coated with Drug Containing Layer of e.g. Agar," KYOT, Jul. 10, 1987.

Lab Prod. Ethiques Ethypharm., "Coated Microgranules Containing a Gastric Protoon Pump Inhibitor witih Two Hydrophobic Materials, Free From Alkali and Any Ionic Surfactant," Derwent Publications Ltd., Ethi. May 21, 1999.

Lakatos L., "Immunology of Inflammatory Bowel Diseases," Acta Physiological Hungarica., vol. 87 (4), pp. 355-372, 2000.

Marteau et al., "Potential of Using Lactic Acid Bacteria for Therapy and Immunomodulation in Man," FEMS Microbiologoy Reviews 12, 1993, pp. 207-220.

McBrearty et al., "Probiotic Bifidobacteria and Their Identification Using Molecular Genetic Techniques," Teagasc, Dairy Products Research Centre, Moorepark, Fermoy, Co. Cork, Ireland Department of Microbiology, University College Cork, Ireland.

McCarthy et al., "Double Blind, Placebo Controlled Trial of Two Probiotic Strains in Interleukin 10 Knockout Mice and Mechanistic Link with Cytokine Balance," Gastroenterology, vol. 122, nr. 4, suppl. 1, pp. A389-A390, DDW Meeting Abstract, Nr. T962.

McCracken et al., "Probiotics and the Immune System.".

McGee et al., "A Synergistic Relationship Between TNF-x, IL-1B, and TGF-Bl on IL-6 Secretion by the IEC-6 Intestinal Epithelial Cell Line," Immunology, 1995, 86, pp. 611.

McKay, et al., "The Effect of Retarded Growth Upon the Length of Lifespan and Upon Ultimate Body Size," J. Nutr., vol. 10, pp. 63-79, 1935.

McKay et al., "Review article: In Vitro Models in Inflammatory Bowel Disease," Aliment Pharmacol. Ther., 1997, 11 (suppl. 3) pp. 70-80.

Medaglini et al., "Mucosal and Systemic Immune Responses to a Recombinant Protein Expressed on the Surface of the Oral Commensal Bacterium Streptococcus gordonii after oral colonization," Proc. Natl. Acad. Sci. USA, vol. 92 pp. 6868-6872, Jul. 1992 Medical Sciences.

Monteleone et al., "Manipulation of Cytokines in the Management of Patients With Inflammatory Bowel Disease," Ann Med., Nov. 2000; 32(8), pp. 552-60.

Morishita Jintan KK, "Capsule Preparation for Enteral Administration of Unsaturated Fatty Acids (Jpn)," Derwent Publications Ltd., MORI, Oct. 30, 1997.

Morishita Jintan KK, "Yogurt for Supply Physiologically Important Intestinal Bacteria—Contains Bacteria Contained in Capsule Having Inner Layer Made of Digestible Substance and Outer Layer Dissolving in Intestine," MORI, Mar. 10, 1995.

O'Callaghan et al., "Differential Cytokine Response of Cells Derived from Different Lymphoid Compartments to Commensal and Pathogenic Bacteria.".

O'Halloran et al., "Adhesion of Potential Probiotic Bacteria to Human Epithelial Cell Lines," Departments of Microbiologoy and Medicine, University College, Mercy Hospital Cork, Ireland, Dept. of Surgery, Mercy Hospital Cork Ireland.

O'Mahony et al., Probiotic Bacteria and Pathogenic Bacteria Elicit Differential Cytokine Responses From Dendritic Cells, XP-001097379.

O'Mahony et al., "Probiotic Impact on Microbial Flora, Inflammation and Tumour Development in IL-10 Knockout Mice," Aliment Pharmacol Ther, 2001, 15, pp. 1219-1225.

O'Mahony et al., "Probiotic Bacteria and the Human Immune System," Dept. Microbiology and Medicine, National Food Biotechnology Centre, University College Cork & Dept. Surgery, Mercy Hospital, Cork Ireland.

Panwala et al., "A Novel Model of Inflammatory Bowel Disease: Mice Deficient for the Multiple Drug Resistance Gene, mdrla, Spontaneously Develop Colitis," The American Association of Immunologists, 1998, The Journal of Immunology, 1998, 161, pp. 5733-5744.

Powrie et al., "Inhibition of the 1 Responses Prevents Inflammatory Bowel Disease in Scid Mice Reconstituted with CD45Rbhi CD4+ T Cells," Immunity, vol. 1, pp. 553-562, Oct. 1994.

Rogler et al., "Cytokines in Inflammatory Bowel Disease," World Journal of Surgery, vol. 22, 1998, pp. 382-389, XP002296948—whole document.

(56) References Cited

OTHER PUBLICATIONS

Roth et al., Ann. NY Acad Sci. 928, pp. 305-315, 2001.
SS Pharmaceutical KK, Tablets Containing Double-Coated Granules-Obtained by Coating with Insol. Polymer, Enteric Polymer and/or Waxes, Then Further Coating with Water or Acid-Soluble Polymer, SSSE, Aug. 18, 1988.
Schmitt et al., "The Immunostimulatory Function of IL-12 in T-Heiper Cell Development and Its Regulation by TGF-B, IFN-y and IL-4," Chem. Immunet Basel Karma, 1997, vol. 68, pp. 70-85.
Shimada, N., "Significance of 1, 5-Anhydro-D-Glucitol in Diabetes Mellitus Management," Sangyo Igaku, 1994, 36(6) pp. 448-449.
Snow Brand Milk Products< "Enteric Capsules—Comprising Core Containing Drug etc. And Coating of Hardened Oil of M. Pt. Higher than Body Temp. And Disintegrated by Lipase in Intestine," SNOW, Mar. 31, 1986.
Soudeyns et al., "The Moving Target: Mechanisms of HIV Persistence During Primary Infection," Immunology Today, Oct. 1999.
Stagg et al., "The Dendritic Cell: It's Role in Intestinal Inflammation and Relationship with Gut Bacteria," www. Gutjnl.com.
Stallmach et al., "Induction and Modulation of Gastrointestinal Inflammation," Trends Immunology Today, Oct. 1998, vol. 19, No. 10, pp. 438-441.
Strober et al., "Reciprocal IFN-gamma and TFG-Beta Responses Regulate the Occurrence of Mucosal Inflammation," Immunol. Today, Feb. 18, 1997, (2) pp. 61-64.
Takeda Chemical Ind KK, "Dry Coated Tablet—Comprises Core Tablets Containing Enzyme Prepn. In Enteric Films Within Outer Shell," TAKE May 10, 1982.
Van Damme et al., "The Proportion of Th 1 Cells, Which Prevail in Cut Mucosa, is Decreased in Inflammatory Bowel Syndrome," 2001, Blackwell Science Ltd. Clinical and Experimental Immunology, 125, pp. 383-390.
Vickers et al., "Comparison of Fermentation of Selected Fructooligosaccharides and Other Fiber Substrates by Canine Colonic Microflora," AJVR, vol. 62, No. 4, Apr. 2001.
Vittorio Scardovi, "Irregular Nonsporing Gram-Positive Rods," Genus Bifidobacterium Orla-Jensen, 1924, 472.
Voet, Donald and Judith G., Biochemistry, John Wilcyl & Sons, Inc. pp. 1044-1045.
Wein et al., "Analyzing a Bioterror Attack on the Food Supply: The Case of Botolinum Toxin in Milk," 2005, The National Academy of Sciences of the USA.
Weindruch and Walford, "The Retardation of Aging and Disease by Dietary Restriction," Springfield, IL: Charles C. Thomas, 1988.
Willott et al., Exp. Neurol. vol. 99(3), pp. 615-621.
Yu, "Modulation of Aging Processes by Dietary Restriction," Boca Raton CRC Press, 94.
Osbaldiston, G.W., et al., "Microflora of Alimentary Tract of Cata", Aermican Journal of Veterinary Research, vol. 32, No. 9, Sep. 1971.
Rastall, R.A., "Bacteria in the Gut: Friends and Foes and How to Alter the Balance", The Journal of Nutrition, vol. 134, No. 8 Suppl, Aug. 2004, pp. 2022S-2026S.
Johnston, K.L., "Small Intestinal Bacterial Overgroth", The Veterinary Clinics of North America. Small Animal Practice, vol. 29, No. 2, Mar. 1999, pp. 523-550.
Aga, Abstracts, Gastroenterology, 116(4) (1999).
Arai et al., Cytokines: Coordinates of Immune and Inflammatory Responses. Annu. Rev. Biochem., 90: 783-836 (1990).
Barbara et al., A role for inflammation in irritable bowel syndrome. Gut, 51: i41-i44 (2002).
Dunne et al., Probiotics: From Myth to Reality. Demonstrations of Functionality in Animal Models of Disease and in Human Clinical Trials. Antonie Van Leeuwenhoek, 76(1-4): 279-92 (1999).
McBrearty et al., Probiotics Bifidobacteria and Their Identification Using Molecular Genetic Techniques, p. 97-107. In J. Buttriss and M. Saltmarsh (ed.), Functional foods: claims and evidence. Royal Society of Chemistry, Cambridge, United Kingdom (2000).
McCarthy et al., Double Bind Placebo Controlled Trial of Two Probiotic Stains in Interleukin 10 Knockout Mice and Mechanistic Link with Cytokine Balance. Gastroenterology, 122(4): Suppl 1, A389-90, DDW Meeting Abstract, Nr. T962 (2003).
McCracken et al., Probiotics and the Immune System (1999).
O'Callaghan et al., Differential Cytokine Response of Cells Derived from Different Lymphoid Compartments to Commensal and Pathogenic Bacteria. Gastroenterology, 124(4): Suppl. 1, A339 (2003).
O'Halloran et al., Adhesion of Potential Probiotic Bacteria to Human Epithelial Cell Lines. Department of Microbiology and Medicine, University College, Mercy Hospital Cork, Ireland, Dept. Of Surgery, Mercy Hospital Cork Ireland, International Dairy Journal, 8: 596 (1998).
O'Mahony et al., Probiotics Bacteria and Pathogenic Bacteria Elicit Differential Cytokine Responses from Dendritic Cells, XP-001097379, Gastroenterology, 120(5): Suppl. 1, A315 (2001).
O'Mahony et al., Probiotic Bacteria and the Human Immune System, Dept. Microbiology and Medicine, National Food Biotechnology Centre, University College Cork & Dept. Surgery, Mercy Hospital, Cork Ireland, Functional Foods Claims and Evidence, J. Royal Chem. Soc., (2002).
Stagg et al., The Dendritic Cell: Its Role in Intestinal Inflammation and Relationship with Gut Bacteria. Gut, 52: 1522-9 (2003).
Voet, Donald and Judith G., Biochemistry, $3^{rd}$ Edition, John Willey & Sons, Inc. pp. 1044-1045 (2004).
Willott et al., Exp. Neurol. 99(3): 615-62 (1988).
Yu, "Modulation of Agin Processes by Dietary Restriction," Boca Raton CRC Press, 94 (1994).
Massi et al., NCBI Genbank Accession No. AB102854, NCBI Genbank (1994).
Rodtong and Tannock, NCBI Genbank Accession No. AF080100, NCBI Genbank (1998).
Mentula, et al., "Comparison Between Cultured Small-Intestinal and Fecal Microbiotas in Beagle Dogs", Applied and Environmental Microbiology, Aug. 2005, vol. 71, No. 8, p. 4169-4175.
Mermelstein, "Novel Dryer Uses Refractance Window Principle", Food Technology, 51(10), p. 96, 1997.
Meyer, et al., "Long-Term Caloric Restriction Ameliorates the Decline in Diastolic Function in Humans", J. Am. College of Cardiology, vol. 47(2), pp. 398-402 (2006).
Mitsuoka, et al., "Ecology of the Bifidobacteria.", The American Journal of Clinical Nutrition, Nov. 1977, vol. 30, pp. 1799-1810.
Mohamed, et al., "Effect of Long-Term Ovariectomy and Estrogen Replacement on the Expression of Estrogen Receptor Gene in Female Rats", Eur J. Endocrinol., 15, 142:307-14, 2000.
Moustafa, et al., "Effects of aging and antioxidants on glucose transport in rat adipocytes", Gerontology, 1995, 41 (6):301-7.
Murphy, et al., "Evaluation and Characterisation of Probiotic Therapy in the CD45RB Transfer Model of Colitis", AGA Abstracts, Gastroenterology, vol. 116, No. 4.
Naaz, et al., "THe Soy Isoflavone Genistein Decreases Adipose Deposition in Mice", Endocrinology, 144 (8)3315-3320, 2003.
Naveh, et al., "Detailed Avocado Pulp Reduces Body Weight and Total Hepatic Fat but Increases Plasma Chloesterol in Male Rats fed Diets with Cholesterol", Am. Soc. for Nutritional Sciences, 2002, 2015-2018.
Nordal, et al., "Isolation of Mannoheptulose and Identification of its Phosphate in Avocado Leaves", J. Am. Chem. Soc., 1954, vol. 76, No. 20, pp. 5054-5055.
Nordal, et al., "Isolation of Mannoheptulose and Identification of its Phosphate in Avocado Leaves", Meddelelser fra Norsk Farmaceutisk Selskap, (1955), 17, 207-213.
Novogrodsky, et al., "Lymphocyte Transformation Induced by Concanavalin A and its Reversion by methyl-alpha-D-mannopyranoside", Biochim. Biophys. Acta, 1971, 228, 579-583.
O'Callaghan, et al., "Human Cytokine Production by Mesenteric Lymph Node Cells in Response to Probiotic and Pathogenic Bacteria", Gastroenterology, vol. 111, No. 4, Suppl. 1., pp. A389-S390 DDW Meeting Abstract No. T962, XP09036733.
Ojewole, et al., "Cardiovascular Effects of Persea Americana Mill (Lauraceae)(avocado) aqueous Leaf Extract in Experimental Animals", Cardiovasc. J. Afr., 2007, 18, pp. 69-76.
O'Mahony, et al., "Probiotic Human Bifidobacteria: Selection of a New Strain and Evaluation in Vitro and In Vivo", Gastroenterology, vol. 118, No. 4, Apr. 2000.

(56) References Cited

OTHER PUBLICATIONS

Park, et al., "Species Specific Oligonucleotide probes for the detection and identification of Lactobacillus isolated from mouse feces", Journal of Applied Microbiology, 2005, vol. 99, pp. 51-57, XP002447051.
Pawelec, et al., "T Cell Immunosenescence In Vitro and In Vivo", Exp. Gerontol, 1999, 34: 419-429.
Pelicano, et al., "Glycolysis Inhibition for Anticancer Treatment", Oncogene, 2006, 25, pp. 4633-4646.
Perlmann, et al., "Inhibition of Cytotoxicity of Lymphocytes by Concanavalin A in vitro", Science, 1970, 168:1112-1115,.
Poehlman, et al., "Caloric Restriction Mimetics: Physical Activity and Body Composition Changes", Journal of Gerontology, Series A 2001, vol. 56A (Special Issue I):45-54.
Purina, "Advancing Life Through Diet Restriction", The Purina Pet Institute Symposium, 2002.
Ramsey, et al., "Dietary Restriction and Aging in Rehesus Monkeys: The University of Wisconsin Study", Experimental Gerontology, 35 (2000) 1131-1149.
Raonimalala, et al., "Action of Soluble Carbohydrates from Avocado Fruit on Utilization of Calcium in the Rat", Ann. Nutr Aliment, 34(4), 734-744, 1980.
Reid, et al., "Prevention of Urinary Tract Infection in Rats with an Indigenous Lactobacillus Casei Strain", Infection and Immunity, 1985, 49(2), pp. 320-324.
Rezek, et al., "Glucose Antimetabolites and Hunger", J. Nutr., 106:143-157 (1976).
Rezek, et al., "Insulin Dependence of Paradoxical Overeating: Effect of Mannoheptulose, Somatostatin, and Cycloheximide", The American Physiological Society, 1979, E205-E211.
Ridker, et al., "C-Reactive Protein, the Metabolic Syndrome and Risk of Incident Cardiovascular Events: An 8-Year Follow-up of 14,719 Initially Healthy American Women", Circulation, vol. 107, No. 3, pp. 391-397.
Riquelme, et al., "Regulation of Carbohydrate Metabolism by 2,5-Anhydro-D-Mannitol", PNAS, 80, pp. 4301-4305 (1983).
Robey, et al., "Akt, Hexokinase, mTOR: Targeting Cellular Energy Metabloism for Cancer Therapy", Drug Discovery Today: Disease Mechanisms, vol. 2, No. 2, 2005, pp. 239-246.
Roe, et al., "Further Studies of the Physiological Availability of Heptoses", J. Biol. Chem., 121:37-43, 1937.
Roe, et al., "The Utilization of D-Mannoheptulose by Adult Rabbits", J. of Biological Chemistry, 112, 443-449, Jan. 1, 1936.
Roth, et al., "Caloric Restriction in Primates and Relevance to Humans", Ann. NY Acad. Aci., 928: 305-315, 2001.
Rowland, et al., "Physiological and Behavioral Responses to Glucoprivation in the Golden Hamster", Physiology and Behavior, vol. 30, No. 5, May 1, 1983, pp. 747-747.
Ruscetti, et al., "Release of Colony-Stimulating Activity from Thymus-Derived Lymphocytes", J Clin Invest. 1975;55(3):520-527.
Sakata, et al., "Feeding Modulation by Pentose and Hexose Analogues", Am. J. Clin. Nutr., 1992, 55:272-277S.
Sayegh, et al., "Impact of Hormone Replacement Therapy on the Body Mass and Fat Compositions of Menopausal Women: A Cross-Sectional Study", Menopause, 6:312-315, 1999.
Scarbrough, et al., "2-Deoxy-D-Glucose and 17-(allylaminio)-17-demethoxygeldanamycin Enhances Toxicity as wella s Increases Parameters Indicative of Oxidative Stress", Free Radical Biology and Medicine, vol. 43, suppl. 1, Nov. 14, 2007, p. S59.
Scardovi, et al., "Deoxyribonucleic Acid Homology Relationships Among Species of the Genus Bifidobacterium", Int. J. Syst. Bacteriol., vol. 21, pp. 276-294, 1971.
Schrek, et al., "Characterizatoin of the B Lymphocyte Response to Pokeweed Mitogen", Annals of Clinical and Laboratory Science, vol. 12, Issue 6, pp. 455-462.
Scrimshaw, et al., "Interactions of Nutrition and Infection", Am. J. Med. Sci., 1959, 237: 367-403.
Scruel, et al., "Interference of D-Mannoheptuloase with D-Glucose phosphorylation, Metabolism, and Functional Effects: Comparison between Liver, Parotid Cells and Pancreatic Islets", Molecular and Cellular Biochemistry, 187, pp. 113-120, 1998.
Sener, et al., "D-Mannoheptulose Uptake and Its Metabolic and Secretory Effects in Human Pancreatic Islets", International Journal of Molecular Medicine, 6:617-620, 2000.
Sener, et al., "Environmental Modulation of D-Fructose Insulinotropic Action", Acta Diabetol, 1998, 35, pp. 74-76.
Shaw, et al., "High Performance Liquid Chromatographic Analysis of d-manno-heptulose, perseitol, glucose and Fructose in Avocado Cultivars", J. Agric. Food Chem., 1980, 28, 279-382.
Silva De Ruiz, et al., "Effect of Lactobacilli and Antibiotics on E. coli Urinary Infections in Mice", Biol. Pharm. Bull., 1996, 19(1): 88-93.
Simon, et al., "Insulin and Proinsulin Secretion and Action", Israel J. Med. Sci., vol. 8, No. 6, Jun. 1972.
Simon, et al., "Metabolism of Mannoheptulose in the Rat. I. Diabetogenic Action", Arch. Biochem. Biophys., 69, pp. 592-601 (1957).
Simons, et al., "2-deoxy-D-glucose (2DG) Enhances Cispalatin Cytotoxicity in Human Head and Neck Cancer Cells Via Metabolic Oxidative Stress", Free Radical Biology and Medicine, vol. 41, No. 1, Nov. 15, 2006, pp. S112-S113.
Simpson, et al., "Genomic Diversity and Relatedness of Bifidobacteria isolated from a Porcine Cecum", Journal of Bacteriology, Apr. 2003, vol. 185, pp. 2571-2581.
Sols, et al., "Substrate Specificity of Brain Hexokinase", Biol. Chem. 210, pp. 581-595 (1954).
Sung, et al., "The Sphincter of Oddi is a Boundary for Bacterial Colonization in the Feline Biliary Tract", Microbial Ecology in Health and Disease, 1990, vol. 3, pp. 199-207.
Sunvold, et al., "Dietary Fiber for Dogs: IV. In Vitro Fermentation of Selected Fiber Sources by Dog Fecal Inoculum and In Vivo Digestion and Metabolism of Fiber-Supplemented Diets", J. Anim. Sci., vol. 73, 1995, 1099-1109.
Sutton, et al., "Considerations for Successful Development and Launch of Personalized Nutrigenomic Foods", Mutation Research, vol. 622, No. 1-2, Aug. 8, 2007, pp. 117-121.
Tesfay, et al., "Anti-Oxidant Levels in Various Tissues During the Maturation of "Hass" Avocado", Journal of Horticultural Science and Biotechnology, 85(2): 106-112.
Trovatelli, et al., "Presence of Bifidobacteria in the Rumen of Calves Fed Different Rations", Appl. Environ. Microbiol., 1976, vol. 32(6), pp. 470-473.
Valente, et al., "Immunologic Function in the Elderly After Injury— The Neutrophil and Innate Immunity", The Journal of Trauma Injury, Infection and Critical Care, vol. 67, No. 5, pp. 968-974, Nov. 2009.
Viktora, et al., "Effect of Ingested Mannoheptulose in Animals and Man", Metabolism, 18(2), 87-102, 1969.
Walker-Bone, et al., "Natural Remedies in the Treatment of Osteoarthritis", Drugs and Aging, 2003, 20(7), pp. 517-526.
Wamelink, et al., "Detection of Transaldolase Deficiency by Quantification of Novel Seven-Carbon Chain Carbohydrate Biomarkers in Urine", J. Inherit. Metab. Dis., (2007), 30, pp. 735-742.
Wan, et al., "Dietary Supplementation with 2-deoxy-d-Glucose Improves Cardiovascular and Neuroendocrine Stress Adaptation in Rats", Am. J. Physiol. Hear. Cir. Physiol, 287: H1186-H1193, 2004.
Weindruch, "The Retardation of Aging by Caloric Restriction", Toxicol. Pathol., 1996, 24:742.
Winnock, et al., "Correlation Between GABA Release from Rat Islet beta-cells and their Metabolic State", Am. J. Physiol Endocrinol. Metab., 282: E937-E942, 2002.
Wood, et al., "Evidence for Insulin Involvement in Arginine- and Glucose-Induced Hypercalciuria in Rat", J. Nutr., 113, pp. 1561-1567, 1983.
Yaeshima, et al., "Bifidobacterium globosum, Subjective Synonym of Bifidobacterium pseudolongum, and Descrption of Bifidobacterium pseudolongum subsp. pseudolongum com. nov. and Bifidobacterium psuedolongum subsp. globosum comb. nov.", Systematic and Applied Microbiology, 1992, vol. 15(3), pp. 380-385.

(56) References Cited

OTHER PUBLICATIONS

Yamamoto, et al., "Changes in Behavior and Gene Expression Induced by Caloric Restriction in C57BL/6 Mice", Physiological Genomics, vol. 39, No. 3, Sep. 8, 2009, pp. 227-235.
Yang, et al., "The Role of Voltage-Gated Calcium Channels in Pancreatic [beta]-Cell Physiology and Pathophysiology", Endocrine Reviews, vol. 27, No. 6, Oct. 1, 2006.
Yu, "Aging and Oxidative Stress: Modulation by Dietary Restriction", Free Radical Biology and Medicine, vol. 21, No. 5, pp. 651-668, 1996.
Zhang, et al., "Dissimilar Effects of D-Mannoheptulose on the phosphorylation of alpha vs beta-D-glucose by either Hexokinase or Glucokinase", International Journal of Molecular Medicine, 14, pp. 107-112, 2004.
All Office Actions, U.S. Appl. No. 09/950,052 (now abandoned).
All Office Actions, U.S. Appl. No. 10/842,300.
All Office Actions, U.S. Appl. No. 11/313,198 (now abandoned).
All Office Actions, U.S. Appl. No. 11/313,199 (now abandoned).
All Office Actions, U.S. Appl. No. 12/012,317.
All Office Actions, U.S. Appl. No. 12/082,710.
All Office Actions, U.S. Appl. No. 12/168,400.
All Office Actions, U.S. Appl. No. 12/371,101.
All Office Actions, U.S. Appl. No. 12/371,266.
All Office Actions, U.S. Appl. No. 12/638,128.
All Office Actions, U.S. Appl. No. 12/716,533.
All Office Actions, U.S. Appl. No. 12/762,539.
All Office Actions, U.S. Appl. No. 12/939,594.
All Office Actions, U.S. Appl. No. 13/098,741.
All Office Actions, U.S. Appl. No. 13/098,756.
All Office Actions, U.S. Appl. No. 14/043,142.
Amendment in response to Nonfinal Office Action mailed Aug. 16, 2011 and issued in connection with U.S. Appl. No. 12/716,540 dated Nov. 15, 2011.
Amendment in response to Nonfinal Office Action mailed Jun. 10, 2011 and issued in connection with U.S. Appl. No. 12/638,101, Dated Sep. 2, 2011.
Amendment in response to Nonfinal Office Action mailed Jun. 7, 2011 and issued in connection with U.S. Appl. No. 12/716,518 dated Oct. 7, 2011.
Amendment in response to Nonfinal office Action mailed Jun. 9, 2011 and issued in connection with U.S. Appl. No. 12/716,562, dated Sep. 2, 2011.
Archived pages from HTTP://web.archive.org for http://medtechnologies.com dated Feb. 2003.
Blue Buffalo Life Protection Formula_package.pdf, http//www.bluebuff.com/products/dogs/lp-adult-chick.shtml Information accessed Feb. 3, 2009.
Breeders Choice, AvoDERM product brochures http://www.breeders-choice.com/about/brochures.htm, Information accessed Feb. 3, 2009.
European Search Report Received in Connection with EP 04 81 5182, mailed on Jun. 13, 2008.
European Search Report Received in Connection with EP 04 81 5186, mailed on Jan. 7, 2013.
Final Office Action issued in connection with U.S. Appl. No. 12/638,101, mailed Dec. 30, 2011.
Final Office Action issued in connection with U.S. Appl. No. 12/716,518 mailed Jan. 4, 2012.
Final Office Action issued in connection with U.S. Appl. No. 12/716,540 mailed Jan. 10, 2012.
Final Office Action issued in connection with U.S. Appl. No. 12/716,562 mailed Dec. 29, 2011.
International Search Report for PCT/US2011/058861, dated Feb. 10, 2012.
International Search Report for PCT/US2012/035921, dated Jul. 10, 2012.
International Search Report for PCT/US2012/036035, dated Jul. 11, 2012.
International Search Report Received in Connection with PCT/IB2008/050382, mailed on Oct. 7, 2008.
International Search Report Received in Connection with PCT/US2004/043068, mailed on Sep. 25, 2007.
Natures Logic Natural Chicken Dinner Fare FROZEN_package.pdf http://www.natureslogic.com/products/ dp_rf_chi.html, Information accessed Feb. 3, 2009.
Natures Logic Natural Chicken Meal_package.pdf http://www.natureslogic.com/products/dp_dry_chi.html, Information accessed Feb. 3, 2009.
Nonfinal Office Action issued in connection with U.S. Appl. No. 12/638,101, mailed Jun. 10, 2011.
Nonfinal Office Action issued in connection with U.S. Appl. No. 12/716,540, mailed Aug. 16, 2011.
Nonfinal Office Action issued in connection with U.S. Appl. No. 12/716,562, mailed Jun. 9, 2011.
Nonfinal Office Action issued in connection with U.S. Appl. No. 12/716,518 mailed Jun. 7, 2011.
Physician's Desk Reference, 1963 Edition, Medical Economics, Inc. Oradell, N.J., 1962, Product Identification Section, SEction Four, p. VIII and XI.
Publication downloaded from http://en.wikipedia.org/wiki/Noni on May 14, 2009, 9 pages.
Supplemental Amendment in response to Nonfinal Office Action mailed Jun. 10, 201, and issued in connection with U.S. Appl. No. 12/638,101, dated Sep. 29, 2011.
LabScan XE User's Manual, Manual Version 1.2, A60-1010-862, Jan. 2003, 53 pp.
"A Balanced Diet", Waltham Book of Dog and Cat Nutrition, Ed. ATB, Edney, Chapter by A. Rainbird, pp. 57-74, Pergamon Press, Oxford.
"Changing Times", The Kiplinger Magazine, vol. 31, No. 1, Jan. 1977, pp. 39-40.
"Kidney Stones in Adults (http://kidney.niddk.nih.gov, pp. 1-14).".
"Lactobacillus animalis genes for 16S-23S intergenic spacer region, 23S ribosomal RNA, strain", Database EMBL: JCM 5670, Jul. 9, 2004, XP002447038.
"Lactobacillus murinus genes for 16S-23S intergenic spacer regions, 23S ribosomal RNA, strain: JCM 1717", Database EMBL, Jul. 9, 2004, XP002447039.
"Mice and Rats", (www.petswarehouse.com, pp. 1-5).
"Nutrient Profiles for Dog Foods", Association of American Feed Control Officials Incorporated, pp. 110-119, 1994.
"Probiotic Basics", (www.usprobiotics.org.basics/, p. 1-12).
"Urinary Tract Infections in Adults", (http://kidney.niddk.nih.gov, pp. 1-11).
Adeyemi, et al., "Analgesic and Anti-Inflammatory Effects of the Aqueous Extract Leaves of Persea America Mill (Lauraceae)", Fitoterapia, IDB Holdings, Milan, IT, vol. 73, No. 5, Aug. 1, 2002, pp. 375-380, XP002318086.
Alves-Filho, Drying Technology, 2002, vol. 20, No. 8, pp. 1541-1557, abstract.
Anderson, et al., Nutrition Reviews, vol. 61, No. 5, pp. S17-S26, May 2003.
Anonymous, "The Best Ever Guacamole—Again, Whole Foods Market", Jan. 18, 2013, Retrieved from the Internet: URL:http://www.wholefoodsmarket.com/blog/best-ever-guacamole-again, p. 3.
Apgar, et al., "Effect of feeding Various Levels of Bifidobacterium globosum A on the Performance, Gastrointestinal Measurements and Immunity of Weanling Pigs and on the Perfromance and Carcass Measurements of Gorwing-Finishing Pigs", J. Animal Science, 1993, vol. 71, pp. 2173-2179.
Appelboom, et al., "Symptoms Modifying Effect of Avocoda/Soybean Unsaponfiables (ASU) in Knee Arthritis. A Double Blind, Prospective, Placebo-Controlled Study", Scandinavian Journal of Rheumatology, vol. 30, pp. 242-247 (2001).
Arany, et al., "The Effect of Carcinogens and Non-Carcinogens on Some Biochemical Features of the Mouse Lung Tissue", Arch. Toxicol., Suppl. 4, 73 (1980).
Asahara, et al., "Antimicrobial Activity of Intraurethrally Adminstered Probiotic Lactobacillus casei in a Murine Model of *Escherichia coli* Urinary Tract Infection", Antimicrobial Agents & Chemotherapy, 2001, 45(6): 1751-1760.

(56) References Cited

OTHER PUBLICATIONS

Ashcroft, et al., "Glucose Metabolism in Mouse Pancreatic Islets", Biochem. J. (1970), 118, pp. 143-154.
Au, et al., "Avocado Soybean Unsaponifiables (ASU) suppress TNF-a, IL-1b, cox-2, iNOS Gene Expression, and Prostaglandin E2 and Nitric Oxide Production in Articular Chondrocytes and Monocyte/Macrophages", Osteoarthritis and Cartilage, 2007, 15, 18 pages.
Balkau, et al., "Insulin resistance: an independent risk factor for cardiovascular disease?", Diabetes Obes. Metab., 1 (Suppl. 1), pp. S23-31, 1999.
Barge, "Avocados May Help Prevent Oral Cancer, OSU Study Shows", Journal of Dental Hygiene, vol. 82, No. 2, Apr. 2008, 3 pp.
Barrows, et al., "Diet and Nutrition", Walleye Culture Manual, R. C. Summerfelt, editor, NCRAC Culture Series 101, North Central Regional Aquaculture Center Publications Office, Iowa State University, Ames.
Begbie, et al., "The Isolation of Some Heptoses, Heptuloses, Octuloses and Nonuloses from Pimula Officinalis JACQ", Carbohydrate Research, 1966, vol. 2, pp. 272-288.
Benno, et al "Individual and Seasonal Variations in the Composition of Fecal Microflora of Beagle Dogs", Bifidobactena Microflora, vol. 11, No. 2, pp. 69-76, 1992.
Biavati, et al., "Electrophoretic Patterns of Proteins in the Genus Bifidobacterium and Proposal of Four New Species", Journal Int. J. Syst. Bacteriol., vol. 32, pp. 358-373, 1982.
Blatherwick, et al., "Metabolism of D-Mannoheptulose. Excretion of the Sugar After Eating Avocado", J. Biol. Chem., vol. 133, pp. 643-650 1940.
Board, et al., "High KM Glucose Phosphorylating (Glucokinase) Activities in a Range of Tumor Cell Lines and Inhibition of Rates of Tumor Growth by the Specific Enzyme Inhibitor Mannoheptulose", Cancer Research, vol. 55, pp. 3278-3285, Aug. 1995.
Botterweck, et al., "Intake of Butylated Hydroxyanisole and Butylated Hydroxytoluene and Stomach Cancer Risk: Results from Analyses in the Netherlands Cohort Study", Food and Chemical Toxicology, 38 (2000, 599-605.
Brai, et al., "Hypoglycemic and Hypocholesterolemic Potential of Persea Americana Leaf Extracts", J. Med. Food, 2007, pp. 356-360.
Bredif, et al., "Avocado Sugars are Effective Inducer of Cutaneous Defensive Functions", Journal of the American Academy of Dermatology, St. Loius, MO, vol. 50, No. 2, Feb. 1, 2007, p. AB84, XP005937005.
Bridigidi, et al., "Specific Detection of Bifidobacterium Strains in a Pharmaceutical Probiotic Product and in Human Feces by Polymerase Chain Reaction", System Appl. Microbial., 23, 2000, 391-399.
Brown, et al., "Glucose Phosphorylation is Essential for the Turnover of Neutral Lipid and the Second Stage Assembly of Triacylglycerol-Rich ApoB-Containing Lipoproteins in Primary Hepatocyte Cultures", American Heart Association, Inc., 1999, pp. 321-329.
Burger, et al., "Cardiomyopathy in Ostriches (Struthio Camelus) Due to Avocado (Persea Americana Var. Guatemalensis) Intoxication", Journal of the South African Veterinary Association, vol. Jaargang 65, No. 2, Jun. 1994.
Campieri, et al., "Reduction of Oxaluria after an Oral Course of Lactic Acid bacteria at High Concentration", Kidney International (2001) Vol. 60, pp. 1097-1105.
Carranza, et al., "Lower Quantities of Avocado as Daily Source of Monounsaturated Fats: Effect on Serum and Membrane Lipids, Endothelial Function, Platelet Aggregation and C-Reactive Protein in Patients with Metabolic Syndrome", Database Embase, Elsevier Science Publishers, Amsterdam NL, Nov. 2004, XP002485347.
Chan, et al., "Ultra Structural and Secretory Heterogeneity of fa/fa (Zucker) Rat Islets", Molecular and Cellular Endocrinology, 136, 1998, pp. 119-129.
Chen, et al., "Action of 5-Thio-D-Glucose and Its 1-Phosphate with Hexokinase and Phosphoglucomutase", Arch. Biochem. Biophys. 169, pp. 392-396 (1975).
Chiricolo, et al., "Cell Adhesion Molecules CD11a and CD18 in Blood Monocytes in Old Age and the Consequences for Immunological Dysfunction", Gerontology, 1995, 41(4), pp. 227-234.
Collins, et al., "A Randomised Controlled Trial of a Probiotic Lactobacillus Strain in Healthy Adults: Assessment of its Delivery, Transit and Influence on Microbial Flora and Enteric Immunity", Microbial Ecology in Health and Disease, vol. 14, No. 2, Jun. 2002, pp. 81-89.
Conde, et al., "OeMST2 Encodes a Monosaccharide Transporter Expressed throughout Olive Fruit Maturation", Plant Cell Physiol., 48(9), pp. 1299-1308, 2007.
Cooke, et al., "Role of Estrogens in Adipocyte Development and Function", Exp. Biol. Med., 229:1127-35, 2004.
Crane, et al., "The Non-Competitive Inhibition of Brain Hexokinase by Glucose-6-Phosphate and Related Compounds", Biol. Chem., 210, pp. 597-696 (1954).
Cruzen, et al., "Effects of Caloric Restriction on Cardiovascular Aging in Non-Human Primates and Humans", Clin. Geriatr. Med., vol. 25(4), pp. 733-743, Nov. 2009.
Cullen, et al., "Inhibition of Glucose Metabolism in Pancreatic Cancer Induces Cytotoxicity via Metabolic Oxidative Stress", Gastroenterology, vol. 128, No. 4, sup. 2, Apr. 2005, pp. A483, XP002495963.
De Pergola, "The Adipose Tissue Metabolism: Role of Testosterone and Dehydroepiandrosterone", Int. J. Obesity, 24: S59-S63, 2000.
Dent, et al., "Lactobacillus animalis JCM5670", Database JCM Catalogue, Japan Collection of Microorganisms, 1986, XP002447035.
Dreau, et al., "Effects of 2-deoxy-D-glucose Adminstration on Immune Parameters in Mice", Immunopharmacology, vol. 39, Jun. 1, 1998, pp. 201-213.
Ekor, et al., "Protective Effect of the Methanolic Leaf Extract of Persea Americana (avocado) Against Paracetamol-Induced acute Hepatoxicity in Rats", International Journal of Pharmacology, vol. 2, No. 4, Jan. 1, 2006, pp. 416-420 XP001538905.
Ernst, "Avocado-Soybean Unsaponitiables (ASU) for Osteoarthritis-A systemic Review", Clin. Rheumatol., 2003, 22, pp. 285-288.
Facchini, et al., "Insulin Resistance as a Predictor of Age-Related Diseases", The Journal of Clinical Endocrinology & Metabolism, 86(8): 3574-3578.
Fajans, et al., "Stimulation of Insulin Release in the Dog by a Nonmetabolizable Amino Acid. Comparison with Leucine and Arginine", J. of Clinical Endocrinology and Metabolism, 33(1) 35-41, Jul. 1971.
Fontana, et al., "Long-term Calorie Restriction is Highly Effective in Reducing the Risk for Artherosclerosis in Humans", PNAS, vol. 101(17), pp. 6659-6663 (2004).
Francesconi, et al., "5-Thio-D-Glucose: Hypothermic Responses in Mice", Am. J. Physiology, 239(3), R214-R218.
Frech, et al., "The Utility of Nutraceuticals in the Treatment of Osteoarthritis", Current Rheumatology Reports, 2007, 9, pp. 25-30.
Gallagher, et al., "The Effects of Traditional Antidiabetic Plants on In Vitro Glucose Diffusion", Nutrition Research, 23 (2003), pp. 413-424.
Gartrell, et al., "The Effects of Chocolate and Chocolate by-product Consumption on Wild and Domestic Animals", Chocolate in Health and Nutrition, Humana Press, 2013, pp. 135-141.
Miller, et al., "2-Deoxy-D-Glucose-Induced Metabolic Stress Enhances Resistance to Listeria monocytogenes Infection in Mice", Physiology & Behavior, vol. 65., No. 3, pp. 535-543, 1998, 1998, 535-543.
Miller, et al., "The Metabolic Stressor 2-Deoxy-D-Glucose (2-DG) Enhances LPS-Stimulated Cytokine Production in Mice", Brain, Behavior, and Immunity, 1993, vol. 7, pp. 317-325, 1993, 317-325.
Ogawa, Journal of Japan Mibyou System Association, 2004, vol. 10, No. 1, p. 140-142 (with machine translation), 2004, 140-142.
Takayanagi, J. Nippon Med. Sch., 2003, vol. 70, No. 1, p. 71 (with machine translation), 2003, 71.
Vasconcelos, et al., "Antagonistic and Protective Effects Against Salmonella enterica Serovar Typhimurium by Lactobacillus murinus in the Digestive Tract of Gnotobiotic Mice", Brazilian Journal of Microbiology (2003) 34 (Supple. 1): 21-24.

(56) References Cited

OTHER PUBLICATIONS

German, et al., "Glucose Sensing in Pancreatic Islet Beta Cells: The Key Role of Glucokinase and the Glycolytic Intermediates", Proc. Nat. Acad. Sci., 90, 1781-1785 (1993).
Gielkens, et al., "Effects of Hyperglycemia and Hyperinsulinemia on Satiety in Humans", Metabolism, vol. 47, No. 3, pp. 321-324, 1998.
Goldrosen, et al., "Impaired Lymphocyte Blastogenic Response in Patients with Colon Adenocarcinoma: Effects of Disease and Age", Journal of Surgical Oncology, 9:229-234, 1977.
Golkar, et al., "Apigenin Inhibits Pancreatic Cancel Cell Proliferation via Down-Regulation of the GLUT-1 Glucose Transporter", Gastroenterology, vol. 130, No. 4, Jul. 22, 2006.
Gondwe, "Effects of Persea Americana Mill (Lauraceae) Ethanolic Leaf Extract on Blood Glucose and Kidney Function in Streptozotocin-Induced Diabetic Rats and on Kidney Cell Lines of the Proximal (LLC-PK1) and Distal Tubules (MDBK)", Methods Find Exp Clin. Pharmacol., 2008, 30(1), pp. 25-35.
Grajales-Lagunes, et al., "Stability and Sensory Quality of Spray Dried Avocado Paste", Drying Technology, vol. 17, No. 1&2, 1999, pp. 317-326.
Greetham, et al., "Bacteriology of the labrador dog gut: A cultural and genotype approach", J. Appl. Microbiol., M:640-646, 2002.
Guo, et al., "In Vivo 2-Deoxyglucose Administration Preserves Glucose and Glutamate Trasport and Mitochondrial Function in Cortical Synaptic Terminals after Exposure to Amyloid Beta-Peptide and Iron: Evidence for a Stress Response", Experimental Neurology, vol. 166., No. 1, Jan. 1, 2000, XP008056810, pp. 173-179.
Hammarstrom, et al., "Mitogenic Leukoagglutinin from Phaseolus vulgaris Binds to a Pentasaccharide Unit in N-acetyllactosamine-type Glycoprotein Glycans", Proc. Natl. Acad. Sci. USA, 79, 1611-1615 (1982).
Hemme, et al., "Lactobacillus murinus JCM1717", Database JCM Catalogue, Japan Collection of Microorganisms, 1982, XP002447036.
Henrotin, et al., "Pharmaceutical and Nutraceutical Management of Canine Osteoarthritis: Present and Future Perspectives", The Veterinary Journal, 170 (2005), pp. 113-123.
Hershkovitz, et al., "Ethylene regulation of Avocado Ripening Differs Between Seeded and Seedless Fruit", Postharvest Biology and Technology, vol. 56, No. 2, May 1, 2010, pp. 138-146.
Hillsvet, "Hill's Presciption Diet, A New Way to Define Pet Obesity", Internet Article, http://www.hillsvet.com/conference-documents/Weight_Management/Therapeutic?Weight_Reduction_Program/BFI_Backgrounder.pdf.
Hoffman, et al., "Diabetogenic Action of 5-Thio-D-glucopyranose in Rats", Biochemistry, vol. 7, pp. 4479-4483 (1968).
Isolauri, et al., "Probiotics: A Role in the Treatment of Intestinal Infection and Inflammation?", Gut, 2002, 50 (Suppl III), pp. iii54-iii59.
Issekutz, et al., "Effect of Mannoheptulose on Glucose Kinetics in Normal and Glucocorticoid Treated Dogs", Life Sciences, 15(4), pp. 635-643, 1974.
Jay, et al., "Metabolic Stability of 3-O-Methyl-D-Glucose in Brain and Other Tissues", J. Neurochem., 55, pp. 989-1000 (1990).
Johnson, et al., "Glucose-Dependent Modulation in Insulin Secretion and Intracellular Calcium Ions by GKA50, a Glucokinase Activator", Diabetes, vol. 56, Jun. 2007, pp. 1694-1702.
Kalani, et al., "Effects of Caloric Restriction and Exercise on Age-Related, Chronic Inflammation Assessed by C-Reactive Protein and Interleukin-6", J. Gerontol. A. Bio. Sci. Med. Sci., vol. 61(3), pp. 211-217 (2006).
Kappler-Tanudyaya, et al., "Combination of Biotransformation and Chromatography for the Isolation and Purification of Mannoheptulose", Biotechnology J. 2007, 2, 692-699.
Katzmarzyk, "The Metabolic Syndrome: An Introduction", Appl. Physiol Nutr. Metab., 32, pp. 1-3 (2007).
Kaufman, et al., "Identification and Quantification of Bifidobacterium Species Isolated from Food with Genus-Specific 16S rRNA-Targeted Probes by Colony Hybridization and PCR", Appl. Environ. Microbiol., Apr. 1997, vol. 63, pp. 1268-1273.
Kealy, et al., "Effects of Diet Restriction on Life Span and Age-Related Changes in Dogs", JAVMA, vol. 220, No. 9, May 1, 2002.
Kibenge, et al., "Identification of Biochemical Defects in Pancreatic Islets of fa/fa Rats", Obesity Research, 3(2), pp. 171-178, Mar. 1995.
Klain, et al., "Mannoheptulose and Fatty Acid Synthesis in the Rat", The Journal of Nutrition, pp. 473-477, 1974.
Koh, et al., "Effects of Mannoheptulose on Lipid Metabolism of Rats", J. Nutr., vol. 104, pp. 1227-1233, 1974.
Koizumi, et al., "Influences of Dietary Restriction and Age on Liver Enzyme Activities and Lipid Peroxidation in Mice", American Institute of Nutrition, Jul. 1986.
Koizumi, et al., "Influences of Dietary Restriction and Age on Liver Enzyme Activities and Lipid Peroxidation in Mice", J. Nutr., 117: 361-367, 1987.
Kok, et al., "Specific Detection and Analysis of a Probiotic Bifidobacterium Strain in Intact Feces", Applied and Environmental Microbiology, 1996, vol. 62, pp. 3668-3672.
Kudo, et al., "An Electron Microscopic Study on Bifidobacterium Pseudolongum SS-24 with Extracellular Material and Naked Bifidobacterium Thermophilum SS-19", AJAS, vol. 2, No. 3, pp. 444-445, 1989.
Kurata, et al., "Structural Evaluation of Glucose Analogues on Feeding Elicitation in Rat", Metabolism, vol. 38, No. 1 (Jan. 1989): pp. 46-51.
La Forge, "Absorption and Effect of Ingested Mannoheptulose", Nutrition Reviews, 1969, vol. 27, No. 7, pp. 206-208.
La Forge, "D-Mannoketoheptose, A New Sugar from the Avocado", J. Biol. Chem. 28:511-22, 1917.
Lane, et al., "2-Deoxy-D-Glucose Feeding in Rats Mimics Physiologic Effects of Calorie Restriction", Journal of Anti-Aging Medicine, vol. 1, No. 4, pp. 327-337, 1998.
Lane, et al., "Calorie Restriction in Nonhuman Primates: Implications for Age-Related Disease Risk", Journal of Anti-Aging Medicine, vol. 1, No. 4, pp. 315-326, 1998.
Lane, et al., "Calorie Restriction Lowers Body Temperature in Rhesus Monkeys, Consistent with a Postulated Anti-Aging Mechanisms in Rodents", PNAS, vol. 93, pp. 4159-4164, Apr. 1996.
Langhans et al. "Changes in Food Intake and Meal Patterns Following Injection of D-Mannoheptulose in Rats", Behavioral and Neural Biology, 38, pp. 269-286 (1983).
Leblond-Bourget, et al., "16S rRNA and 16S to 23S Internal Transcribed Spacer Sequence Analysis Reveal Inter- and Intraspecific Bifidobacterium Phylogeny", International Journal of Systemic Bacteriology, vol. 6, No. 1, Jan. 1996, pp. 102-111.
Leclercq-Meyer, et aL, "Effects of D-mannoheptulose And Its Hexaacetate Ester On Hormonal Secretion From The Perfused Pancreas", International Journal of Molecular Medicine, 2000, vol. 6, pp. 143-152.
Lee, "Medicinal Plant Composition Suitable for Each Blood Type", WPI/Thomson, vol. 2004, No. 46, Mar. 22, 2004.
Libby, "Inflammatory mechanisms: the molecular basis of inflammation and disease", Nutr. Rev., Dec 2007, 65 (12 Pt. 2): S140-6.
Liu, et al. "Hass Avocado Carbohydrate Fluctuations. I. Growth and Phenology", J. Amer. Soc. Hod. Sci., 124(6): 671-675, 1999.
Liu, et al. "Hass Avocado Carbohydrate Fluctuations. II. Fruit Growth and Ripening", J. Amer. Soc. Hort. Sci., 124(6): 676-681 (1999).
Liu, et al. "Postulated Physiological Roles of the Seven Carbon Sugars, Mannoheptulose, and perseitol in Avocado", J. Amer. Soc. Hort. Sci., 127(1):108-114, 2002.
Maklashina, et al., "Is Defective Electron Transport at the Hub of Aging", Aging Cell, vol. 3, 21-27, 2004.
Mamula, et al., Gastrointestinal Tract Infections—Chapter 11. 2004, pp. 79-89.
Masoro, et al., "Dietary Restriction Alters Characteristics of Glucose Fuel Use", Journal of Gerontology, Biological Sciences, 1992, vol. 47, No. 6, B202-B208.

(56) References Cited

OTHER PUBLICATIONS

Masoro, "Overview of Caloric Restriction and Aging", Mech. Aging Dev., vol. 126, pp. 913-922 (2005).

Mattarelli, et al., "Characterization of the plasmid pVS809 from Bifidobacterium globosum", Microbiologica, 1994, vol. 17, pp. 327-331.

Mattson, et al., "Beneficial Effects of Intermittent Fasting and Caloric Restriction on the Cardiovascular and Cerebrovascular Systems", J. Nutr, Biol. 16, 3:129-137, 2005.

Seikagaku jiten (third edition), Tokyo Kagaku Dojin Publishing Co., Inc., 1998, pp. 657-658.

* cited by examiner

SEQUENCE LISTING

```
<160> NUMBER OF SEQ ID NOS: 5

<210> SEQ ID NO 1
<211> LENGTH: 269
<212> TYPE: DNA
<213> ORGANISM: Lactobacillus salivarius subsp. salicinius
<220> FEATURE:
<221> NAME/KEY: misc_feature
<222> LOCATION: (13)..(14)
<223> OTHER INFORMATION: n is a, c, g, or t
<220> FEATURE:
<221> NAME/KEY: misc_feature
<222> LOCATION: (18)..(18)
<223> OTHER INFORMATION: n is a, c, g, or t
<220> FEATURE:
<221> NAME/KEY: misc_feature
<222> LOCATION: (21)..(21)
<223> OTHER INFORMATION: n is a, c, g, or t
<220> FEATURE:
<221> NAME/KEY: misc_feature
<222> LOCATION: (26)..(26)
```

<223> OTHER INFORMATION: n is a, c, g, or t
<220> FEATURE:
<221> NAME/KEY: misc_feature
<222> LOCATION: (28)..(28)
<223> OTHER INFORMATION: n is a, c, g, or t
<220> FEATURE:
<221> NAME/KEY: misc_feature
<222> LOCATION: (43)..(43)
<223> OTHER INFORMATION: n is a, c, g, or t
<220> FEATURE:
<221> NAME/KEY: misc_feature
<222> LOCATION: (65)..(65)
<223> OTHER INFORMATION: n is a, c, g, or t
<220> FEATURE:
<221> NAME/KEY: misc_feature
<222> LOCATION: (121)..(122)
<223> OTHER INFORMATION: n is a, c, g, or t
<220> FEATURE:
<221> NAME/KEY: misc_feature
<222> LOCATION: (124)..(124)
<223> OTHER INFORMATION: n is a, c, g, or t
<220> FEATURE:
<221> NAME/KEY: misc_feature
<222> LOCATION: (166)..(166)
<223> OTHER INFORMATION: n is a, c, g, or t
<220> FEATURE:
<221> NAME/KEY: misc_feature
<222> LOCATION: (225)..(225)
<223> OTHER INFORMATION: n is a, c, g, or t
<220> FEATURE:
<221> NAME/KEY: misc_feature
<222> LOCATION: (255)..(255)
<223> OTHER INFORMATION: n is a, c, g, or t
<220> FEATURE:
<221> NAME/KEY: misc_feature
<222> LOCATION: (267)..(267)
<223> OTHER INFORMATION: n is a, c, g, or t

<400> SEQUENCE: 1
ttgcgggatc acnncctntc naaggnanaa ttacggaacc tgnacattta tcggatactt      60
tgttnagttt tgagaggtca tatctctcaa gattttgttc tttgaaaact agatattgat     120
nnanttctta aaataaaacc gagaacaccg cgttttaaag agtttnaaac aagaattata     180
gttcttaatc gctaaactca taacctatta tcgttagata atatnaggtt aagttattaa     240
gggcgtatgg tggangcctt ggccccnga                                       269

<210> SEQ ID NO 2
<211> LENGTH: 255
<212> TYPE: DNA
<213> ORGANISM: Lactobacillus animalis
<220> FEATURE:
<221> NAME/KEY: misc_feature
<222> LOCATION: (2)..(2)
<223> OTHER INFORMATION: n is a, c, g, or t
<220> FEATURE:
<221> NAME/KEY: misc_feature
<222> LOCATION: (6)..(6)
<223> OTHER INFORMATION: n is a, c, g, or t
<220> FEATURE:
<221> NAME/KEY: misc_feature
<222> LOCATION: (12)..(12)
<223> OTHER INFORMATION: n is a, c, g, or t
<220> FEATURE:
<221> NAME/KEY: misc_feature
<222> LOCATION: (14)..(14)
<223> OTHER INFORMATION: n is a, c, g, or t
<220> FEATURE:
<221> NAME/KEY: misc_feature
<222> LOCATION: (24)..(24)
<223> OTHER INFORMATION: n is a, c, g, or t
<220> FEATURE:
<221> NAME/KEY: misc_feature
<222> LOCATION: (50)..(50)
<223> OTHER INFORMATION: n is a, c, g, or t

```
<220> FEATURE:
<221> NAME/KEY: misc_feature
<222> LOCATION: (52)..(52)
<223> OTHER INFORMATION: n is a, c, g, or t
<220> FEATURE:
<221> NAME/KEY: misc_feature
<222> LOCATION: (60)..(60)
<223> OTHER INFORMATION: n is a, c, g, or t
<220> FEATURE:
<221> NAME/KEY: misc_feature
<222> LOCATION: (114)..(115)
<223> OTHER INFORMATION: n is a, c, g, or t
<220> FEATURE:
<221> NAME/KEY: misc_feature
<222> LOCATION: (117)..(117)
<223> OTHER INFORMATION: n is a, c, g, or t
<220> FEATURE:
<221> NAME/KEY: misc_feature
<222> LOCATION: (120)..(120)
<223> OTHER INFORMATION: n is a, c, g, or t
<220> FEATURE:
<221> NAME/KEY: misc_feature
<222> LOCATION: (123)..(123)
<223> OTHER INFORMATION: n is a, c, g, or t
<220> FEATURE:
<221> NAME/KEY: misc_feature
<222> LOCATION: (186)..(186)
<223> OTHER INFORMATION: n is a, c, g, or t
<220> FEATURE:
<221> NAME/KEY: misc_feature
<222> LOCATION: (208)..(208)
<223> OTHER INFORMATION: n is a, c, g, or t
<220> FEATURE:
<221> NAME/KEY: misc_feature
<222> LOCATION: (232)..(232)
<223> OTHER INFORMATION: n is a, c, g, or t
<220> FEATURE:
<221> NAME/KEY: misc_feature
<222> LOCATION: (240)..(240)
<223> OTHER INFORMATION: n is a, c, g, or t
<220> FEATURE:
<221> NAME/KEY: misc_feature
<222> LOCATION: (249)..(249)
<223> OTHER INFORMATION: n is a, c, g, or t
<220> FEATURE:
<221> NAME/KEY: misc_feature
<222> LOCATION: (252)..(252)
<223> OTHER INFORMATION: n is a, c, g, or t

<400> SEQUENCE: 2
cncctnactt ancnccattt atcntacgat aatggttatg agtttagcgn tnaaacattn      60
atgttttaaa ctctttaaaa cgcggtgttc tcggttattt taattaacaa aganntnaan    120
ganattatct agtttcaaa gaacaagttt gagagtagac ctctcaaaac taaacaaagt     180
tcacgntaaa gtgcaggttt ccgaaatnat ccttagaaag gaggtgagcc ancagagaan   240
ggaggtganc cngca                                                       255

<210> SEQ ID NO 3
<211> LENGTH: 284
<212> TYPE: DNA
<213> ORGANISM: Lactobacillus reuteri
<220> FEATURE:
<221> NAME/KEY: misc_feature
<222> LOCATION: (121)..(121)
<223> OTHER INFORMATION: n is a, c, g, or t
<220> FEATURE:
<221> NAME/KEY: misc_feature
<222> LOCATION: (265)..(265)
<223> OTHER INFORMATION: n is a, c, g, or t
<220> FEATURE:
<221> NAME/KEY: misc_feature
<222> LOCATION: (268)..(268)
<223> OTHER INFORMATION: n is a, c, g, or t
<220> FEATURE:
```

```
<221> NAME/KEY: misc_feature
<222> LOCATION: (274)..(274)
<223> OTHER INFORMATION: n is a, c, g, or t
<220> FEATURE:
<221> NAME/KEY: misc_feature
<222> LOCATION: (276)..(276)
<223> OTHER INFORMATION: n is a, c, g, or t

<400> SEQUENCE: 3
gggtctgctg gatcacctcc tttctaagga ataaaacgga acctacacat cgaagaaact      60
ttgtttagtt ttgaggggtt taccctcaga gcttgtactt tgaaaactaa atactatcgt     120
natttcttta ttaacaaaac aataaaccga gaacaccgcg ttatttgagt tttaattaac     180
gaattataat cgctaactca attaatcaga caatctttga ttgtttgggt taagttatga     240
agggcgcatg gtggatgcct tggcnccnga gccncnagac caga                     284

<210> SEQ ID NO 4
<211> LENGTH: 18
<212> TYPE: DNA
<213> ORGANISM: Artificial
<220> FEATURE:
<223> OTHER INFORMATION: PCR Primer sequence

<400> SEQUENCE: 4
gctggatcac ctcctttc                                                   18

<210> SEQ ID NO 5
<211> LENGTH: 18
<212> TYPE: DNA
<213> ORGANISM: Artificial
<220> FEATURE:
<223> OTHER INFORMATION: PCR Primer sequence

<400> SEQUENCE: 5
ctggtgccaa ggcatcca                                                   18
```

FELINE PROBIOTIC LACTOBACILLI COMPOSITION AND METHODS

CROSS REFERENCE TO RELATED APPLICATIONS

This application claims the benefit of U.S. Provisional Application No. 60/686,055, filed May 31, 2005 and U.S. Provisional Application No. 60/692,440, filed Jun. 21, 2005.

FIELD OF THE INVENTION

The present invention relates to the field of probiotic micro-organisms, more specifically feline probiotic lactic acid bacteria and methods of use.

BACKGROUND OF THE INVENTION

The defense mechanisms to protect the mammalian gastrointestinal (GI) tract from colonisation by bacteria are highly complex. The GI tract of most mammals are colonised by native microflora, and invasive pathogenic micro-organisms. In a healthy state, these competing microflora are in a state of equilibrium. Modification of the intestinal microflora equilibrium may lead to or prevent many GI disorders, both in humans, and other mammalian species, such as companion animals including cats, dogs and rabbits. The well being of companion animals is closely related to their feeding and GI health, and maintenance of the intestinal microflora equilibrium in these animals may result in healthier companion animals.

The number and composition of the intestinal microflora tend to be stable, although age and diet may modify it. Gastric acidity, bile, intestinal peristalsis and local immunity are factors thought to be important in the regulation of bacterial flora in the small intestine of human beings and various other mammals. Often companion animal GI disorders, including those found in felines, are linked to bacterial overgrowth and the production of enterotoxins by pathogenic bacteria. These factors disrupt the intestinal microflora equilibrium and can promote inflammation and aberrant immune responses.

During the last few years, research has begun to highlight some valuable strains of bacteria and their potential use as probiotic agents. Probiotics are considered to be preparations of bacteria, either viable or dead, their constituents such as proteins or carbohydrates, or purified fractions of bacterial ferments that promote mammalian health by preserving the natural microflora in the GI tract, and reinforcing the normal controls on aberrant immune responses. It is believed by some that probiotic bacteria are more effective when derived from the species, or closely related species, intended to be treated. Therefore, there is a need for probiotic strains derived from companion animals to be used for companion animals, that are different to those derived from humans.

WO 01/90311 discloses probiotic micro-organisms isolated from faecal samples obtained from cats having probiotic activity. However, these bacteria were obtained from faecal samples, and may not form part of the natural intestinal microflora present in the upper portion of the GI tract.

Consequently, there is a need to provide strains of bacteria obtainable by isolation from the natural intestinal microflora present in the upper portion of the GI tract that are particularly adapted for cats, and have been selected for their probiotic properties and ability to survive processing, and to incorporate these strains into compositions that are suitable for their use.

SUMMARY OF THE INVENTION

According to the invention there is provided strains of lactic acid bacteria of the genus *Lactobacilli* obtainable by isolation from resected and washed feline gastrointestinal tract having a probiotic activity in animals. The lactic acid bacterial strains are preferably selected from the species *Lactobacillus salivarius, Lactobacillus animalis, Lactobacillus reuteri, Lactobacillus acidophilus, Lactobacillus johnsonni Lactobacillus brevis, Lactobacillus bulgaricus, Lactobacillus casei, Lactobacillus cellobiosus, Lactobacillus curvatus, Lactobacillus delbruekii, Lactobacillus fermentum, Lactobacillus helveticus, Lactobacillus lactis,* or *Lactobacillus plantarum.*

In a preferred embodiment, the strain of lactic acid bacteria is selected from the group comprising *Lactobacilli*, having a 16s-23s polynucleotide sequence having greater than 94% homology to SEQ. ID NO. 1, greater than 93% homology to SEQ. ID NO. 2, or greater than 98% homology to SEQ. ID NO. 3.

In a further preferred embodiment, the lactic acid bacterial strain is selected from the group comprising *Lactobacillus salivarius* ss *salicinius* NCIMB 41287 (AHF 122A), *Lactobacillus animalis* NCIMB 41288 (AHF 223C), *Lactobacillus reuteri* NCIMB 41289 (AHF 5119) or a mutant thereof.

Furthermore, the present invention is directed towards providing uses of lactic acid bacteria obtainable by isolation from resected and washed feline gastrointestinal tract for maintaining and improving companion animal health, and compositions comprising the lactic acid bacteria.

These and other features, aspects, and advantages of the present invention will become evident to those skilled in the art from a reading of the present disclosure.

SEQUENCES

SEQ. ID NO. 1—16s-23s intergenic spacer nucleotide sequence from *Lactobacillus salivarius* subsp. *Salicinius*, NCIMB 41287

SEQ. ID NO. 2—16s-23s intergenic spacer nucleotide sequence from *Lactobacillus animalis*, NCIMB 41288

SEQ. ID NO. 3—16s-23s intergenic spacer nucleotide sequence from *Lactobacillus reuteri*, NCIMB 41289

SEQ. ID NO. 4—Left 16s-23s PCR primer sequence for sequence analysis.

SEQ. ID NO. 5—Right 16s-23s PCR primer sequence for sequence analysis.

Bacterial Deposit Numbers

The table below indicates *Lactobacillus* species and strain number for strains that are examples of the present invention. The bacterial strains are deposited with the National Collections of Industrial Food and Marine Bacteria (NCIMB), Aberdeen, UK.

| Strain | Deposit Number | 16 s–23s Sequence |
|---|---|---|
| *Lactobacillus salivarius* subsp. *salicinius* | NCIMB 41287 | SEQ. ID NO. 1 |
| *Lactobacillus animalis* | NCIMB 41288 | SEQ. ID NO. 2 |
| *Lactobacillus reuteri* | NCIMB 41289 | SEQ. ID NO. 3 |

DETAILED DESCRIPTION OF THE INVENTION

All weights, measurements and concentrations herein are measured at 25° C. on the composition in its entirety, unless otherwise specified.

Unless otherwise indicated, all percentages of compositions referred to herein are weight percentages and all ratios are weight ratios.

Unless otherwise indicated, all molecular weights are weight average molecular weights.

Unless otherwise indicated, the content of all literature sources referred to within this text are incorporated herein in full by reference.

Except where specific examples of actual measured values are presented, numerical values referred to herein should be considered to be qualified by the word "about".

Within the following description, the abbreviation CFU ("colony-forming unit") designates the number of bacterial cells revealed by microbiological counts on agar plates, as will be commonly understood in the art.

As used herein, the term "mutants thereof" includes derived bacterial strains comprising DNA mutations in other DNA sequences in the bacterial genome excluding the 16s-23s intergenic sequence.

As used herein, the term "DNA mutations" includes natural or induced mutations comprising at least single base alterations including deletions, insertions, transversions, and other DNA modifications known to those skilled in the art, including genetic modification introduced into a parent nucleotide or amino acid sequence whilst maintaining at least 50% homology to the parent sequence. Preferably, the sequence comprising the DNA mutation or mutations has at least 60%, more preferably at least 75%, more preferably still 85% homology with the parental sequence. As used herein, sequence "homology" can be determined using standard techniques known to those skilled in the art. For example, homology may be determined using the on-line homology algorithm "BLAST" program, publicly available at http://www.ncbi.nlm.nih.gov/BLAST/.

As used herein "genetic modification" includes the introduction of exogenous and/or endogenous DNA sequences into the genome of an organism either by insertion into the genome of said organism or by vectors including plasmid DNA or bacteriophage as known by one skilled in the art, said DNA sequence being at least two deoxyribonucleic acid bases in length.

As used herein, "companion animal" means a domestic animal. Preferably, "companion animal" means a domestic feline (cat), canine (dog), rabbit, ferret, horse, cow, or the like. More preferably, "companion animal" means a domestic feline.

Lactic Acid *Lactobacilli* Strains

The first aspect of the present invention comprises a strain of lactic acid bacteria of the genus *Lactobacilli* obtainable by isolation from resected and washed feline gastrointestinal tract having probiotic activity in animals. Probiotics are micro-organisms, either viable or dead, processed compositions of micro-organisms, their constituents such as proteins or carbohydrates, or purified fractions of bacterial ferments that beneficially affect a host. The general use of probiotic bacteria is in the form of viable cells. However, it can be extended to non-viable cells such as killed cultures or compositions containing beneficial factors expressed by the probiotic bacteria. This may include thermally killed micro-organisms, or micro-organisms killed by exposure to altered pH or subjected to pressure. For the purpose of the present invention, "probiotics" is further intended to include the metabolites generated by the micro-organisms of the present invention during fermentation, if they are not separately indicated. These metabolites may be released to the medium of fermentation, or they may be stored within the micro-organism. As used herein "probiotic" also includes bacteria, bacterial homogenates, bacterial proteins, bacterial extracts, bacterial ferment supernatants, and mixtures thereof, which perform beneficial functions to the host animal when given at a therapeutic dose.

It has been found that lactic acid bacteria of the genus *Lactobacilli* obtainable by isolation directly from resected and washed GI tract of mammals are adherent to the GI tract following feeding of viable bacterial cells, and are also significantly immunomodulatory when fed to animals in viable, non-viable or fractionated form. Without being bound by theory, it is believed that *Lactobacilli* obtainable by isolation from resected and washed GI tract closely associate with the gut mucosal tissues. Without further being bound by theory, this is believed to result in the probiotic *Lactobacilli* of the present invention generating alternative host responses that result in its probiotic action. It has been found that probiotic bacteria obtainable by isolation from resected and washed GI tract can modulate the host's immune system via direct interaction with the mucosal epithelium, and the host's immune cells. This immunomodulation, in conjunction with the traditional mechanism of action associated with probiotic bacteria, i.e. the prevention of pathogen adherence to the gut by occlusion and competition for nutrients, results in the *Lactobacilli* of the present invention being highly efficacious as a probiotic organism.

The *Lactobacilli* of the present invention, obtainable by isolation from resected and washed feline GI tract, have in vitro anti-microbial activity against a number of pathogenic bacterial strains/species. Without being bound by theory, it is believed that this in vitro anti-microbial activity is indicative of potential probiotic activity in vivo in animals, preferably companion animals such as felines. The lactic acid bacteria of the present invention preferably have in vitro anti-microbial activity against *Salmonella typhimurium*, *Listeria monocytogenes*, *Listeria innocua* or *Eschericia coli*, more preferably a mixture of these strains, more preferably still, all of these strains.

Without being bound by theory, it is believed that the anti-microbial activity of the lactic acid bacteria of the present invention may be the result of a number of different actions by the lactic acid bacteria herein. It has previously been suggested in the art that several strains of bacteria isolated from faecal samples exert their probiotic effect in the GI tract following oral consumption by preventing the attachment of pathogenic organisms to the gut mucosa by occlusion. This requires oral consumption of "live" or viable bacterial cells in order for a colony of bacteria to be established in the gut. However, it is believed that the *Lactobacilli* of the present invention, obtainable by isolation from resected and washed feline GI tract, whilst exerting some probiotic effect due to occlusion if given in a viable form, may deliver a substantial probiotic effect in either the viable or non-viable form due to the production during fermentation in vitro of a substance or substances that either inhibit the growth of or kill pathogenic micro-organisms, and/or alter the host animal's immune competence. This form of probiotic activity is desirable, as the bacteria of the present invention can be given as either viable or non-viable cultures or purified fermentation products and still deliver a beneficial therapeutic effect to the host animal.

Preferably, the lactic acid bacteria of the present invention are able to maintain viability following transit through the GI tract. This is desirable in order for live cultures of the bacteria to be taken orally, and for colonisation to occur in the intestines and bowel following transit through the oesophagus and stomach. Colonisation of the intestine and bowel by the lactic acid bacteria of the present invention is desirable for long-term probiotic benefits to be delivered to the host. Oral dosing of non-viable cells or purified isolates thereof induces temporary benefits, but as the bacteria are not viable, they are not able to grow, and continuously deliver a probiotic effect in situ. As a result this may require the host to be dosed regularly in order to maintain the health benefits. In contrast, viable cells that are able to survive gastric transit in the viable form, and subsequently colonise by adhering to and proliferating on the gut mucosa are able to deliver probiotic effects continuously in situ.

Therefore, it is preferable that the lactic acid bacteria of the present invention maintain viability after suspension in a media having a pH of 2.5 for 1 hour. As used herein, "maintain viability" means that at least 25% of the bacteria initially suspended in the test media are viable using the plate count method known to those skilled in the art. Preferably, "maintain viability" means that at least 50% of the bacteria initially suspended are viable. It is desirable for the lactic acid bacteria of the present invention to maintain viability following exposure to low pH as this mimics the exposure to gastric juices in the stomach and upper intestine in vivo following oral consumption in animals.

Furthermore, it is preferable that the lactic acid bacteria of the present invention have a growth of at least 33% when in the presence of at least 0.5% feline bile salts. Growth, as used herein is described in further detail in example 3. More preferably, the bacteria of the present invention have a growth of at least 33% when in the presence of at least 1% feline bile salts. More preferably still, the bacteria of the present invention have a growth of 100% in the presence of 0.5% feline bile salts. Without being bound by theory it is believed that the lactic acid bacteria of the present invention, capable of maintaining viability in the presence of at least 0.5% feline bile salts, are able to survive the conditions present in the intestine. This is thought to be a result of the addition of feline bile to the culture medium mimicking the conditions of the intestine.

Further still, it is preferable that the lactic acid bacteria of the present invention have significant adhesion to gut epithelial cells in vitro. As used herein, "significant adhesion" means at least 1% of the total number of lactic acid bacteria co-incubated with the epithelial cells in vitro adhere to the epithelial cells. More preferably, at least 5% of bacterial cells co-incubated adhere to epithelial cells in vitro. Without wishing to be bound by theory, it is believed that gut epithelial cell adherence in vitro is indicative of the lactic acid bacteria's ability to colonise the GI tract of an animal in vivo.

Preferably, the strain of lactic acid bacteria according to the present invention is of a species selected from the group comprising *Lactobacillus salivarius, Lactobacillus animalis, Lactobacillus reuteri, Lactobacillus acidophilus, Lactobacillus johnsonni Lactobacillus brevis, Lactobacillus bulgaricus, Lactobacillus casei, Lactobacillus cellobiosus, Lactobacillus curvatus, Lactobacillus delbruekii, Lactobacillus fermentum, Lactobacillus helveticus, Lactobacillus lactis,* or *Lactobacillus plantarum*. Preferably, the strain of lactic acid bacteria is selected from the group comprising *Lactobacillus salivarius, Lactobacillus animalis, Lactobacillus reuteri, Lactobacillus acidophilus,* or *Lactobacillus johnsonni*.

The 16s-23s intergenic polynucelotide sequence is known to those skilled in the art as the sequence of DNA in the bacterial genome that can be used in order to identify different species and strains of bacteria. This intergenic polynucelotide sequence can be determined by the method detailed below in example 4.

In a preferred embodiment of the present invention, the strain of lactic acid bacteria is selected from the group comprising *Lactobacilli* having a 16s-23s polynucleotide sequence having greater than 94% homology to SEQ. ID NO. 1, greater than 93% homology to SEQ. ID NO. 2, or greater than 98% homology to SEQ. ID NO. 3. More preferably the strain of lactic acid bacteria is selected from the group comprising *Lactobacilli* having a 16s-23s polynucleotide sequence having greater than 98% homology to SEQ. ID NO. 1, SEQ. ID NO. 2, or SEQ. ID NO. 3. More preferably still, the strain of lactic acid bacteria according to the present invention is selected from the group comprising *Lactobacilli* having a 16s-23s polynucleotide sequence selected from SEQ. ID NO. 1, SEQ. ID NO. 2, or SEQ. ID NO. 3. More preferably still, the strain of lactic acid bacteria according to the present invention is selected from the group comprising *Lactobacillus salivarius* ss *salicinius* NCIMB .41287 (AHF 122A), *Lactobacillus animalis* NCIMB 41288 (AHF 223C), *Lactobacillus reuteri* NCIMB 41289 (AHF 5119) or a mutant thereof.

The strain of lactic acid bacteria of the genus *Lactobacilli* obtainable by isolation from resected and washed feline gastrointestinal tract can be used to deliver probiotic benefit following oral consumption in animals, preferably companion animals or humans. This probiotic benefit generally maintains and improves the overall health of the animal. Non-limiting elements of animal health and physiology that benefit, either in therapeutically relieving the symptoms of, or disease prevention by prophylaxis include inflammatory disorders, immunodeficiency, inflammatory bowel disease, irritable bowel syndrome, cancer (particularly those of the gastrointestinal and immune systems), diarrhoeal disease, antibiotic associated diarrhoea, appendicitis, autoimmune disorders, multiple sclerosis, Alzheimer's disease, amyloidosis, rheumatoid arthritis, arthritis, joint mobility, diabetes mellitus, insulin resistance, bacterial infections, viral infections, fungal infections, periodontal disease, urogenital disease, surgical associated trauma, surgical-induced metastatic disease, sepsis, weight loss, weight gain, excessive adipose tissue accumulation, anorexia, fever control, cachexia, wound healing, ulcers, gut barrier infection, allergy, asthma, respiratory disorders, circulatory disorders, coronary heart disease, anaemia, disorders of the blood coagulation system, renal disease, disorders of the central nervous system, hepatic disease, ischaemia, nutritional disorders, osteoporosis, endocrine disorders, and epidermal disorders. Preferred are treatment of the gastrointestinal tract, including treatment or prevention of diarrhoea; immune system regulation, preferably the treatment or prevention of autoimmune disease and inflammation; maintaining or improving the health of the skin and/or coat system, preferably treating or preventing atopic disease of the skin; ameliorating or reducing the effects of aging, including mental awareness and activity levels; preventing disorders associated with the hypothalamus-pituitary-adrenal axis, and improving joint health whereby improving mobility.

The treatment of the disorders disclosed above may be measured using techniques known to those skilled in the art.

For example, inflammatory disorders including autoimmune disease and inflammation may be detected and monitored using in vivo immune function tests such as lymphocyte blastogenesis, natural killer cell activity, antibody response to vaccines, delayed-type hypersensitivity, and mixtures thereof. Such methods are briefly described herein, but well known to those skilled in the art.

1. Lymphocyte blastogenesis: This assay measures the proliferative response in vitro of lymphocytes isolated from fresh whole blood of test and control animals to various mitogens and is a measure of overall T- and B-cell function. Briefly, peripheral blood mononucleocytes (PBMC) are isolated from whole blood by Ficoll-Hypaque density centrifugation methods known to those skilled in the art. The isolated PBMCs are washed twice in RPMI 1640 cell media supplemented with HEPES, L-glutamine and penicillin/streptomycin. The washed cells are resuspended in RPMI 1640, counted, and the cell density adjusted appropriately. The $2\times10^5$ cells are exposed to a range of concentrations (0.1 µg/ml to 100 µg/ml) of various mitogens, some examples of which include pokeweed mitogen (Gibco), phytohaemagglutinin (Gibco) and conconavalin A (Sigma) in triplicate for 72 hours at 37° C. and 5% $CO_2$ with 10% foetal bovine serum (Sigma). At 54 hours the cells are pulsed with 1 µCi $^3$H-thymidine, and the cells harvested and scintillation counts read on a TopCount NXT at 72 hours.

2. Natural killer cell activity: As described in U.S. Pat. No. 6,310,090, this assay measures the in vitro effector activity of natural killer cells isolated from fresh whole blood of test and control animals. Natural killer cells are a component of the innate immune function of a mammal. Feline thyroid adenocarcinoma cells were used as target cells in assessing NK cell cytotoxic activity. This cell line was previously shown to be susceptible to killing by feline NK cell. Target cells were cultured in a T75 flask with 20 mL minimum essential medium (MEM; Sigma Chem. Co., St. Louis, Mo.) supplemented with 10% fetal calf serum (FCS), 100 U/mL of penicillin and 100 µg/mL of streptomycin. When confluent, target cells were trypsinized, washed 3 times and resuspended to $5\times10^5$ cells/mL in complete medium (RPMI-1640+10% FCS+100 U/mL of penicillin+100 µg/mL of streptomycin). Triplicate 100 µL aliquots of the target cells were pipetted into 96-well U-bottom plates (Costar, Cambridge, Mass.) and incubated for 8 hours to allow cell adherence. Lymphocytes (effector cells; 100.µL) isolated by Ficoll-Hypaque separation (as described above) were then added to the target cells to provide an effector/target cell (E:T) ratio of 10:1. After 10 hours of incubation at 37° C., 20.µl of a substrate containing 5.µg of 3-(4,5-dimethylthiazol-2-yl)-2,5-diphenyltetrazolium bromide (MTT) was added. The mixture was incubated for 4 hours at 37° C. after which the unmetabolized MTT was removed by aspiration. The formazan crystals were dissolved by adding 200 µL of 95% ethanol. Optical density was measured at 570 nm using a microplate reader. The percentage of NK cell-specific lysis was calculated as follows:

$$\text{Specific Cytotoxicity (\%)}=100\times\{1-[(\text{OD of target cells and effector cells}-\text{OD of effector cells})/(\text{OD of target cells})]\}$$

3. Antibody response to vaccines: The test subjects are given an array (up to 5) of vaccines after at least 12 weeks of probiotic or control feeding. The vaccines may be a mixture of novel and redundant vaccines. Non-limiting examples of vaccine arrays that may be used include mixtures of vaccines prepared by Fort Dodge Animal Health. Non-limiting examples of vaccines suitable for use herein include Feline distemper, adenovirus, coronavirus, parainfluenza, and parvovirus. The test subject's vaccine history will determine the vaccines to be used. The specific antibodies to the vaccines given are measured in blood for 3 weeks and the length and strength of response in control and probiotic feeding groups compared.

4. Delayed-type hypersensitivity: An in vivo, non-invasive method of assessing immune system status. This test comprises an intradermal injection of the polyclonal mitogen Phytohemmaglutinin (PHA) in combination with sheep red blood cells a multivalent vaccine, histamine (100 µL of 0.0275 g/L Histamine Phosphate; Greer, Lenoir, N.C.), or PBS (100 µL of Phosphate Buffered Saline, 8.5 g/L; Sigma). The immune response to the antigen is recorded as skinfold thickness using calipers at time intervals of 0, 24, 48 and 72 hours post-injection. An increase in skinfold thickness is indicative of a greater hypersensitivity response that should be decreased by treatment with the bacteria of the present invention.

Additional methods for determining the effect of the *Lactobacilli* bacteria of the present invention are described in U.S. Pat. No. 6,133,323 and U.S. Pat. No. 6,310,090.

Furthermore, ameliorating the effects of age may be determined using dual x-ray absorptometry or CT scan for measuring body composition, including body fat mass, fat-free mass and bone mineral content. Similarly, this method may be used to determine anatomy changes such as weight loss or bone density in subjects following infection.

The *Lactobacilli* of the present invention may also be used in a method for reducing stress levels in companion animals. Concentrations of blood stress hormones including epinephrine, norepinephrine, dopamine, Cortisol, C-reactive protein and other acute phase proteins may be measured to determine stress levels and their reduction or maintenance. These hormones are recognized biomarkers of stress and can be readily measured using techniques known to those skilled in the art. Additionally, direct measure of adrenal size as an in vivo marker of activity of the hypothalamus-pituitary-adrenal axis may be measured by CT imaging.

Further still, maintenance or improvement of the health of the skin and/or coat system of companion animals, including atopic disease of the skin, may be measured using skin and coat assessments conducted by two trained individuals. Examples of criteria examined during such assessments include:

a) Shedding index: A shedding index is assigned to each test subject by collecting hair produced during a standardized brushing session. The hair is retained and weighed, and control and test subjects compared.

b) Subjective skin/coat evaluations: Trained panelists subjectively evaluate skin and coat condition by assessing shedding, dander, shine, uniformity, softness and density.

c) Skin functional assessment: The barrier function of the skin may be assessed by wiping the skin surface with an acetone-soaked gauze. This technique effectively disrupts the skin barrier by removing single cell layers and associated lipid fractions of the stratum corneum. Barrier disruption is quantified by measuring the increase in transepidermal water loss (TEWL) and the degree of redness of the insulted site using methods known to those skilled in the art. Redness (erythema) scores are obtained using the previously described camera and lighting system. TEWL readings and redness scores are obtained immediately before and after disruption, and at five and 24-hour endpoints to assess the protective and healing properties of skin.

The treatment or prevention of diarrhoea in companion animals may be measured using stool scores. Stools scores may be recorded daily according to the following guidelines and control and test groups compared before and after feeding with the bacteria according to the present invention.

Score: 5 Extremely Dry

This stool is hard and does not stick to surfaces. Stool will roll when pushed. No indentations are made when stool is picked up. Stool is often defecated in groups of individual stools instead of one complete unit. The stool maintains original shape after collection.

Score: 4 Firm (Ideal Stool)

This stool is firm, well shaped, and cylindrical. This stool does not break apart easily when picked up. This stool may leave residue on surfaces and gloves. This stool is often defecated as one unit. The stool maintains original shape after collection.

Score: 3 Soft, with Shape

This stool is soft, however there are definite shapes. This stool will break apart easily and will definitely leave residue on surfaces and gloves. The stool often loses original shape after collection. This stool is often present with another score but can comprise whole stool sample.

Score: 2 Soft, without Shape

This stool is soft and will have no cylindrical shape. The shape often associated with a "2" is a "cow patty" shape. This stool will lose the original shape when collected and will definitely leave residue on surfaces and gloves. This stool score is often present with another score but can comprise the whole stool sample. This stool sample may spread over an area of several inches.

Score: 1 Liquid

This stool score will always resemble liquid and there may or may not be particulate matter present. This stool will often be defecated in groups of piles instead of one complete unit. Mucous is often present with this stool sample. This stool sample is very difficult to collect and residue is always left on surfaces and gloves. This stool sample may spread over an area of several inches.

In addition, other observations are also recorded, including: blood in stool; foreign object in stool; or mucous in stool.

Furthermore, the treatment of gastrointestinal infection in companion animals may comprise improving microbial ecology of companion animals. Improving the microbial ecology of companion animals preferably comprises reducing the levels of pathogenic bacteria in the faeces of companion animals. The levels of pathogenic bacteria present in the faeces of companion animals may be enumerated using the standard plate count method known to those skilled in the art. More preferably, the pathogenic bacteria are selected from the group consisting of *Clostridia, Escherichia, Salmonella*, bacteriodes and mixtures thereof. Non-limiting examples of suitable strains of pathogenic bacteria include *C. perfringens, C. difficile, Eschericia coli, Salmonella typhimurium* and mixtures thereof.

The method of use of the bacteria of the present invention may also include the treatment, either prophylactic or therapeutic of the urinary tract of mammals, preferably companion animals. Non-limiting examples of urinary tract treatment include treatment or prevention of urinary tract infections, treatment or prevention of kidney disease, including urinary tract stones, treatment or prevention of bladder infections and the like. Without being bound by theory, it is believed that the *Lactobacilli* bacteria of the present invention are useful in preventing these ailments as a result of their ability to degrade oxalic acid, as demonstrated in vitro. Oxalic acid is a by-product of urinary metabolism that can form insoluble precipitates that result in kidney, bladder and other urinary tract infections. By degrading oxalic acid, and therefore potentially preventing its precipitation and build up in the urinary tract, the bacteria of the present invention may treat and prevent infections and other ailments of the urinary tract. Oxalic acid degradation may be measured in vitro using the Oxalic acid test kit cat #755699 commercially available from Boehringer Mannheim/R-Biopharm.

The *Lactobacilli* of the present invention may be used in a method for improving or maintaining the health of companion animals comprising improving fibre digestion. Improving fibre digestion is desirable as it promotes the growth of said probiotic bacteria, as well as beneficial endogenous microflora, which aid in the suppression of some potentially pathogenic bacteria. In addition, a decrease in the amount of toxic metabolites and detrimental enzymes that result from colonic fermentation has been documented in humans (Tomomatsu, H. "Health effects of oligosaccharides", (1994) *Food Technol,* 48, 61-65). Fibre digestion may be determined using the method described in Vickers et al. (2001), "Comparison of fermentation of selected fructooligosaccharides and other fiber substrates by feline colonic microflora", *Am. J. Vet. Res.* 61 (4), 609-615, with the exception that instead of inoculating using diluted fecal samples each experiment used pure cultures of the bacterial strains of interest.

The feline probiotic strains of the present invention may be used to reduce the odor of the feces and urine and concomitantly in the litterbox by reducing the production of compounds in the feces and urine that cause odor. Non-limiting examples of odor-causing compounds include ammonia, indoles, phenols, amines, branched chain fatty acids, and volatile sulphur-containing compounds. Without wishing to be bound by theory it is believed that reducing the levels o these compounds in the feces or urine of a companion animal reduces the odor associated with the feces or urine. Furthermore, for companion animals that use a litter box, there is a concomitant decrease in litter box odor.

The method of use of the lactic acid bacteria of the present invention typically involves oral consumption by the animal. Oral consumption may take place as part of the normal dietary intake, or as a supplement thereto. The oral consumption typically occurs at least once a month, preferably at least once a week, more preferably at least once per day. The lactic acid bacteria of the present invention may be given to the companion animal in a therapeutically effective amount to maintain or improve the health of the animal, preferably a companion animal. As used herein, the term "therapeutically effective amount" with reference to the lactic acid bacteria, means that amount of the bacteria sufficient to provide the desired effect or benefit to a host animal in need of treatment, yet low enough to avoid adverse effects such as toxicity, irritation, or allergic response, commensurate with a reasonable benefit/risk ratio when used in the manner of the present invention. The specific "therapeutically effective amount" will vary with such factors as the particular condition being treated, the physical condition of the user, the duration of the treatment, the nature of concurrent therapy (if any), the specific dosage form to be used, the carrier employed, the solubility of the dose form, and the particular dosing regimen.

Preferably, the lactic acid bacteria are given to the companion animal at a dose of from 1.0E+04 to 1.0E+14 CFU per day, more preferably from 1.0E+06 to 1.0E+12 CFU per day. The composition preferably may contain at least 0.001% of from 1.0E+04 to 1.0E+12 CFU/g of the lactic acid bacteria of the genus *Lactobacilli* obtainable by isolation from resected and washed feline GI tract. The lactic acid bacteria can be given to the animal in either viable form, or as killed cells, or distillates, isolates or other fractions of the fermentation products of the lactic acid bacteria of the present invention, or any mixture thereof.

Preferably, the lactic acid bacteria, or a purified or isolated fraction thereof, are used to prepare a composition intended to maintain or improve the health of an animal. As indicated above, the composition may be part of the normal dietary intake, or a supplement. Where the composition comprises part of the normal dietary intake, the composition may be in the form of a dried animal food such as biscuits or kibbles, a processed grain feed, a wet animal food, yoghurts, gravies, chews, treats and the like.

Such compositions may comprise further components. Other components are beneficial for inclusion in the compositions used herein, but are optional for purposes of the invention. For example, food compositions are preferably nutritionally balanced. In one embodiment, the food compositions may comprise, on a dry matter basis, from about 20% to about 50% crude protein, preferably from about 22% to about 40% crude protein, by weight of the food composition. The crude protein material may comprise any material having a protein content of at least about 15% by weight, non-limiting examples of which include vegetable proteins such as soybean, cotton seed, and peanut, animal proteins such as casein, albumin, and meat tissue. Non-limiting examples of meat tissue useful herein include fresh meat, and dried or rendered meals such as fish meal, poultry meal, meat meal, bone meal and the like. Other types of suitable crude protein sources include wheat gluten or corn gluten, and proteins extracted from microbial sources such as yeast.

Furthermore, the food compositions may comprise, on a dry matter basis, from about 5% to about 35% fat, preferably from about 10% to about 30% fat, by weight of the food composition. Further still, food compositions comprising the lactic acid bacteria of the present invention may also comprise from about 4% to about 25% total dietary fibre. The compositions may also comprise a multiple starch source as described in WO99/51108.

The compositions of the present invention may further comprise a source of carbohydrate. Grains or cereals such as rice, corn, milo, sorghum, barley, alfalfa, wheat, and the like are illustrative sources. In addition, the compositions may also contain other materials such as dried whey and other dairy by products.

The compositions comprising the bacteria of the present invention may also comprise a prebiotic. "Prebiotic" includes substances or compounds that are fermented by the intestinal flora of the companion animal and hence promote the growth or development of lactic acid bacteria in the gastro-intestinal tract of the companion animal at the expense of pathogenic bacteria. The result of this fermentation is a release of fatty acids, in particular short-chain fatty acids in the colon. This has the effect of reducing the pH value in the colon. Non-limiting examples of suitable prebiotics include oligosaccharides, such as inulin and its hydrolysis products commonly known as fructooligosaccharides, galacto-oligosaccharides, xylo-oligosaccharides or oligo derivatives of starch. The prebiotics may be provided in any suitable form. For example, the prebiotic may be provided in the form of plant material which contains the fiber. Suitable plant materials include asparagus, artichokes, onions, wheat or chicory, or residues of these plant materials. Alternatively, the prebiotic fiber may be provided as an inulin extract, for example extracts from chicory are suitable. Suitable inulin extracts may be obtained from Orafti SA of Tirlemont 3300, Belgium under the trade mark "Raftiline". For example, the inulin may be provided in the form of Raftiline (g) ST which is a fine white powder which contains about 90 to about 94% by weight of inulin, up to about 4% by weight of glucose and fructose, and about 4 to 9% by weight of sucrose. Alternatively, the fiber may be in the form of a fructooligosaccharide such as obtained from Orafti SA of Tirlemont 3300, Belgium under the trade mark "Raftilose". For example, the inulin may be provided in the form o Raftilose (g) P95. Otherwise, the fructooligosaccharides may be obtained by hydrolyzing inulin, by enzymatic methods, or by using micro-organisms.

For dried companion animal foods a suitable process is extrusion cooking, although baking and other suitable processes may be used. When extrusion cooked, the dried companion animal food is usually provided in the form of a kibble. If a prebiotic is used, the prebiotic may be admixed with the other ingredients of the dried companion animal food prior to processing. A suitable process is described in European patent application No 0850569. If a probiotic micro-organism is used, the organism is best coated onto or filled into the dried companion animal food. A suitable process is described in European patent publication Number EP 0 862 863.

For wet foods, the processes described in U.S. Pat. Nos. 4,781,939 and 5,132,137 may be used to produce simulated meat products. Other procedures for producing chunk type products may also be used; for example cooking in a steam oven. Alternatively, loaf type products may be produced by emulsifying a suitable meat material to produce a meat emulsion, adding a suitable gelling agent, and heating the meat emulsion prior to filling into cans or other containers. Typical wet food compositions may comprise from about 5% to about 15% protein, from about 1% to about 10% fat, and from about 1% to about 7% fibre. Non-limiting ingredients that may be used in wet food compositions include chicken, turkey, beef, whitefish, chicken broth, turkey broth, beef broth, chicken liver, brewers rice, corn grits, fish meal, egg, beet pulp, chloride, flax meal, lamb, beef by-products, chicken by-products and mixtures thereof.

In another embodiment, supplement compositions such as biscuits, chews, and other treats may comprise, on a dry matter basis, from about 20% to about 60% protein, or from about 22% to about 40% protein, by weight of the supplement composition. As another example, the supplement compositions may comprise, on a dry matter basis, from about 5% to about 35% fat, or from about 10% to about 30% fat, by weight of the supplement composition. Food and supplement compositions intended for use by felines or felines are commonly known in the art.

The companion animal foods may contain other active agents such as long chain fatty acids and zinc. Suitable long chain fatty acids include alpha-linoleic acid, gamma linolenic acid, linoleic acid, eicosapentanoic acid, and docosahexanoic acid. Fish oils are a suitable source of eicosapentanoic acids and docosahexanoic acid.

Borage oil, blackcurrent seed oil and evening primrose oil are suitable sources of gamma linolenic acid. Safflower oils, sunflower oils, corn oils and soy bean oils are suitable sources of linoleic acid. These oils may also be used in the coating substrates referred to above. Zinc may be provided in various suitable forms, for example as zinc sulfate or zinc oxide. Further, many ingredients commonly used in companion animal foods are sources of fatty acids and zinc. It has been observed that the combination of chicory, as a source of prebiotic, with a linoleic-acid rich oil, such as soy bean oil, provides unexpected benefits, suggestive of a synergistic effect.

Where the composition is in the form of a gravy, the composition preferably comprises at least 10% of a broth, or stock, non-limiting examples of which include vegetable beef, chicken or ham stock. Typical gravy compositions may comprise from about 0.5% to about 5% crude protein, from about 2% to about 5% crude fat, and from about 1% to about 5% fibre.

Further non-limiting examples of supplements suitable for use herein include powders, oil suspensions, milk-based suspensions, cheeses, cocoa-butter-based compositions and pills or capsules. Where the composition is in the form of a pill, suitable binding agents are required to maintain the pill in a solid, pressed form. Non-limiting examples of suitable binding agents include the natural gums such as xanthan gum, pectins, lecithins, alginates and others known to those skilled in the art. Where the composition is in the form of a capsule, the composition is preferably encapsulated using technologies known to those skilled in the art. Non-limiting examples of suitable encapsulation materials include polyvinyl alcohol (PVA), polyvinylpyrrolidone (PVP), alginates, and gelatin. Yoghurt-based compositions may comprise from about 1% to about 5% protein, from about 10% to about 20% carbohydrate, from about 1% to about 5% fibre, from about 1% to about 5% fat and from about 50% to about 90% liquid carrier such as milk.

EXAMPLES

The following examples are provided to illustrate the invention and are not intended to limit the scope thereof in any manner.

Example 1

Isolation of Lactic Acid Bacteria from Feline GI Tracts

Feline intestinal samples were obtained from healthy cats presenting at the local veterinarians for owner initiated and approved euthanasia. All animals were healthy and disease-free. The colon, mid-colon, caecum and ileum of each cat were dissected in order to expose the mucosa.

Supernatants were removed following agitation of the mucosal tissue (vortexed for 1 minute) and following mechanical homogenisation of the tissue. Each supernatant was plated on de Mann Rogosa Sharpe (MRS) agar. These were incubated anaerobically, using the Anerocult GasPak system, for 48 hours at 37° C. Isolated colonies from the plates were re-streaked onto either MRS and again grown anaerobically under the same conditions. Isolated colonies were re-streaked a further 4 times in order to purify a single strain. Colony morphology and microscopic appearance were assessed. Suitable isolates were tested for Gram reaction and catalase activity. Identification of gram positive, catalase negative rods was performed using API testing (API 50CHL, BioMerieux). Harvested cells were washed twice with 0.05M phosphate buffer (pH 6.5) and cysteine-HCl (500 mg/l) followed by sonication. Centrifugation removed cellular debris. Supernatants were incubated with NaF (6 mg/ml) and Na iodoacetate (10 mg/ml) for 30 minutes at 37° C. The reaction was stopped by incubation with hydroxylamine HCl (pH 6.5) for 10 minutes at room temperature. Colour development was monitored following the addition of HCl (4M), $FeCl_3.6H_2O$ (5% (w/v) in 0.1M HCl) and fructose-6-phosphate (Na salt). Formation of acetyl phosphate from fructose-6-phosphate was evidenced by the reddish colour formed by the ferric chelate of its hydroxymate.

Example 2

Screening for Anti-Microbial Activity

Each of the isolated lactic acid bacterial strains was incubated anaerobically in MRS broth. 2 µl of each culture were spotted onto MRS agar plates and incubated anaerobically overnight. *Salmonella typhimurium* and Entero Pathogenic *E. Coli* (ExPEC) were pre-grown overnight and 100 µl inoculated into molten agar (1% v/v). This indicator culture was poured onto the surface of the inoculated MRS plates. Following overnight incubation, zones of inhibition around the probiotic colony were measured. All experiments were performed in duplicate on three separate occasions. In addition, incorporating the buffer 2% betaglycerophosphate into the agar enabled assessment of the contribution of acid production to the observed pathogen inhibition in vitro.

The data presented in Table 2 clearly demonstrate that the lactic acid bacteria strains of the present invention obtainable by isolation from resected and washed feline GI tract have significant anti-microbial activity in vitro, indicative of potential probiotic activity.

TABLE 2

|  | AHF122A | AHF223C | AHF5119 |
|---|---|---|---|
| *S. typhimurium* | 9.34 | 7.5 | 9.665 |
| ExPEC | 11.84 | 7.67 | 11.17 |

Example 3

In Vitro Measures of Survival and Colonisation pH Tolerance

Bacterial cells were harvested from overnight cultures, washed twice in phosphate buffer (pH 6.5) and resuspended in MRS/TPY broth adjusted with 1M HCl to pH 2.5. The cells were incubated anaerobically at 37° C. and their survival measured at intervals of 0, 30, 60, 120, 240 and 360 minutes using the plate count method known to those skilled in the art. Table 3 summarises this data per strain.

TABLE 3

Survival of strains in a low pH environment (pH 2.5). All data are log CFU counts.

| | TIME (min) | | | | | |
|---|---|---|---|---|---|---|
| STRAIN | 0 | 30 | 60 | 120 | 180 | 360 |
| NCIMB 41287 | 9.31 | 9.13 | 8.95 | 8.88 | 8.84 | 8.52 |
| NCIMB 41288 | 8.85 | 8.79 | 8.89 | 8.65 | 8.71 | 8.59 |
| NCIMB 41289 | 9.25 | 9.06 | 8.97 | 9.10 | 9.00 | 8.88 |

Bile Resistance

The bacterial strains were streaked onto MRS agar supplemented with porcine bile (Sigma) at 0.5%, 1% and 5% (w/v). Plates were incubated at 37° C. under anaerobic conditions and the growth recorded after 48 hours. Growth was compared with control plates by an experienced observer, and the growth of colonies described as:

Negative (0)—no growth;

+(1)—Hazy translucent growth (<33% control-plates with 0% bile);

++(2)—Definite growth but not as good as controls (>33% but <66%);

+++(3)—Growth equivalent to controls (>66%).

Once the growth of the colonies in the presence of bile salts is compared with the controls, the growth descriptors are given numerical values of 0, 1, 2 or 3 (−; +; ++, +++ respectively), and then expressed as a percentage, where 3 represents 100%.

Table 4 demonstrates that the *Bifidobacterium* of the present invention clearly demonstrate a resistance to bile salts, being able to grow and form colonies at a level of at least 66% in most instances when exposed to 0.3% porcine bile salts.

TABLE 4

Survival of strains in various concentrations of porcine bile

| STRAIN | PERCENTAGE BILE (%) | | | | | | | |
|---|---|---|---|---|---|---|---|---|
| | 0 | 0.3 | 0.5 | 1 | 2 | 5 | 7.5 | 10 |
| NCIMB 41287 | +++ | + | + | − | − | − | − | − |
| NCIMB 41288 | +++ | +++ | +++ | ++ | ++ | ++ | ++ | + |
| NCIMB 41289 | +++ | +++ | +++ | +++ | ++ | ++ | + | + |

Furthermore, in order to assess any differences in the ability of the strains to colonise the GI tract of cats, the bacterial strains were streaked onto MRS agar supplemented with feline bile at 0.5%, 1% and 2% (w/v). Feline bile was obtained from cats undergoing endoscopy in a clinical setting during a non-terminal procedure. Plates were incubated at 37° C. under anaerobic conditions and the growth recorded after 48 hours. Growth was compared with control plates by an experienced observer, and the growth of colonies described as:

Negative (0)—no growth;

+(1)—Hazy translucent growth (<33% control-plates with 0% bile);

++(2)—Definite growth but not as good as controls (>33% but <66%);

+++(3)—Growth equivalent to controls (>66%).

Once the growth of the colonies in the presence of bile salts is compared with the controls, the growth descriptors are given numerical values of 0, 1, 2 or 3 (−; +; ++, +++ respectively), and then expressed as a percentage, where 3 represents 100%.

Table 5 demonstrates that the *Bifidobacterium* of the present invention clearly demonstrate a resistance to feline bile salts, being able to grow and form colonies at a level of at least 66% in most instances when exposed to 0.5% feline bile salts.

TABLE 5

Survival of strains in various concentrations of feline bile

| STRAIN | PERCENTAGE BILE (%) | | | |
|---|---|---|---|---|
| | 0 | 0.5 | 1 | 2 |
| NCIMB 41287 | +++ | +++ | +++ | +++ |
| NCIMB 41288 | +++ | +++ | ++ | ++ |
| NCIMB 41289 | +++ | +++ | +++ | +++ |

Gut Epithelial Cell Adhesion

The human epithelial cell line, HT-29, was used to assess the adhesion properties of selected strains. Epithelial cells were routinely cultured as a monolayer in 75 cm² tissue culture flasks at 37° C. in a humidified atmosphere containing 5% $CO_2$ in Dulbecco's Minimal Essential Media (DMEM) containing 10% foetal calf serum (FCS), pen/strep, glutamine and fungizone. For experimental purposes, the epithelial cells were seeded at a concentration of $5\times10^5$ cells/ml (3 mls total volume) per well in 6 well culture plates (Sarstedt). Following incubation for 7 days, to allow differentiation, the epithelial monolayers were washed with antibiotic-free medium containing 10% FCS. Bacterial suspensions plus/in antibiotic-free DMEM were added to each well and the cells incubated for 90 minutes at 37° C. Following incubation, the monolayers were washed three times with PBS. The epithelial cells were lysed in deionised H2O and the number of adherent bacteria enumerated using the plate count method known to those skilled in the art. Adhesion was expressed as a percentage of the number of bacteria initially plated. *Lactobacillus* AHF122A had an adhesion level of 39.5%, whilst *Lactobacillus* AHF223C had an adhesion level of 13.9%. *Lactobacillus* AHF5119 had an adhesion level of 36.7%.

Example 4

16s-23s Intergenic Polynucleotide Sequencing

The feline *Bifidobacterium* isolates were centrifuged in stock tubes and the resulting pellet lysed in 100 µl of Extraction Solution and 25 µl of Tissue Preparation solution (Sigma, XNAT2 Kit), incubated for 10 minutes at room temperature for 10 minutes. The samples were then incubated for 5 minutes at 95° C. and then 100 µl of Neutralization Solution (XNAT2 kit) was added. The genomic DNA solution was then, quantified using a Nanodrop spectrophotometer and stored at 4° C.

PCR was performed using the intergenic spacer (IGS) primers, IGS L: 5'-GCTGGATCACCTCCTTTC-3' and IGS R: 5'-CTGGTGCCAAGGCATCCA-3' Bridgidi et al 2000, System Appl. Microbiol., 23, 391-399 (2000)). The cycling conditions were 94° C. for 3 min (1 cycle), 94° C. for 30 sec, 53° C. for 30 sec, 72° C. for 30 sec (28 cycles). The PCR reaction contained 4 µl (50 ng) of DNA, PCR mix (XNAT2 kit), 0.4 µM IGS L and R primer (MWG Biotech, Germany). The PCR reactions were performed on an Eppendorf thermocycler. The PCR products (10 µl) were ran alongside a molecular weight marker (100 bp Ladder, Roche) on a 2% agarose EtBr stained gel in TAE, to determine the IGS profile.

PCR products of Bifidobacterium (single band) were purified using the Promega Wizard PCR purification kit.

The purified PCR products were sequenced using the primer sequences (above) for the intergenic spacer region.

Sequence data was the searched against the NCBI nucleotide database to determine the identity of the strain by nucleotide homology.

Following sequencing, the obtained sequences for the four deposited strains were compared with the on-line sequence database "BLAST", available at http://www.ncbi.nlm.nih.gov/BLAST/ for homology with other deposited bacterial 16s-23s sequences. The closest match for AHF122A was the strain *Lactobacillus salivarius* subsp. *Salicinius* (AB102859) with a homology score of 94%. The closest match for AHF223C was *Lactobacillus animalis* strain LA51 (AY526615) with a homology score of 93%. The closest match for AHF5316 was *Lactobacillus reuteri* DSM 20016 (AF080100) with a homology score of 98%.

Example 5

Example Compositions

Examples 1 to 4 are examples of dried kibble compositions comprising the probiotic *Lactobacilli* of the present invention.

|  | Percentage on a weight Basis | | | |
| --- | --- | --- | --- | --- |
| Ingredient | Ex. 1 | Ex. 2 | Ex. 3 | Ex. 4 |
| Cereal grains | To 100 | To 100 | To 100 | To 100 |
| Poultry by-product meal | 43.5 | 40 | 45 | 35 |
| Poultry fat | 1.28 | 1.02 | 1.16 | 1.35 |
| Egg product | 2.4 | 2.1 | 2.5 | 2.2 |
| Chicken liver meal | 1.0 | 1.0 | 1.0 | 1.0 |
| Brewer's dried yeast | 1.0 | 1.0 | 1.0 | 1.0 |
| Monosodium phosphate | 1.0 | 1.0 | 1.0 | 1.0 |
| Calcium carbonate | 0.8 | 0.8 | 0.8 | 0.8 |
| Potassium chloride | 0.6 | 0.6 | 0.6 | 0.6 |
| Vitamins | 0.4 | 0.4 | 0.4 | 0.4 |
| Choline chloride | 0.3 | 0.3 | 0.3 | 0.3 |
| Minerals | 0.3 | 0.3 | 0.3 | 0.3 |
| DL-Methionine | 0.1 | 0.1 | 0.1 | 0.1 |
| Sodium Chloride | 0.03 | 0.03 | 0.03 | 0.03 |
| Probiotic ($1 \times 10^{10}$ cfu/g NCIMB 41287 in sunflower oil) | 1 | 0.5 | — | 0.6 |
| Probiotic ($1 \times 10^{10}$ cfu/g NCIMB 41288 in sunflower oil) | — | 0.5 | 1 | 0.4 |

Examples 5 to 7 are examples of wet companion animal food compositions comprising the probiotic *Lactobacilli* of the present invention.

|  | Percentage on a weight Basis | | |
| --- | --- | --- | --- |
| Ingredient | Ex. 5 | Ex. 6 | Ex. 7 |
| Water | To 38 | To 47 | To 50 |
| Poultry Liver | To 25 | To 20 | To 15 |
| Poultry Products | 25 | 20 | 20 |
| Brewers Rice | 5 | 7 | 10 |
| Egg Product | 3 | 2.5 | 1.5 |
| Poultry Fat | 2.9 | 3.0 | 3.2 |
| Chicken Stock | 0.6 | 0.7 | 0.9 |
| Taurine | 0.1 | 0.1 | 0.1 |
| Vitamins | 0.05 | 0.1 | 0.1 |
| Minerals | 0.05 | 0.1 | 0.1 |
| Probiotic ($1 \times 10^{10}$ cfu/g NCIMB 41289) | 4 | 5 | 6 |

Examples 8 to 10 are examples of yoghurt supplement compositions comprising the probiotic *Lactobacilli* of the present invention.

|  | Percentage on a weight Basis | | |
| --- | --- | --- | --- |
| Ingredient | Ex. 8 | Ex. 9 | Ex. 10 |
| Milk | 38 | 42 | 48 |
| Sugar | 12 | 12 | 10 |
| Modified Starch | 1.0 | 0.8 | 0.8 |
| Prebiotic | 0.25 | 0.3 | 0.5 |
| Probiotic ($1 \times 10^{10}$ cfu/g NCIMB 41287) | 4 | 5 | 6 |

All documents cited in the Detailed Description of the Invention are, are, in relevant part, incorporated herein by reference; the citation of any document is not to be construed as an admission that it is prior art with respect to the present invention.

While particular embodiments of the present invention have been illustrated and described, it would be obvious to those skilled in the art that various other changes and modifications can be made without departing from the spirit and scope of the invention. It is therefore intended to cover in the appended claims all such changes and modifications that are within the scope of this invention.

What is claimed:

1. A composition comprising a biologically purified strain of adherent lactic acid bacteria of the genus *Lactobacilli* isolated from resected and washed feline gastrointestinal tract having probiotic activity, and having the ability to survive and colonize the gastrointestinal tract of a companion animal, wherein said strain is selected from the group consisting of *Lactobacillus salivarius* ss *salicinius* NCIMB 41287 (AHF 122A), *Lactobacillus animalis* NCIMB 41288 (AHF 223C), and *Lactobacillus reuteri* NCIMB 41289 (AHF 5119) and a carrier.

2. The composition according to claim 1, said strain having at least 33% growth when cultured in the presence of 0.5% feline bile salts.

3. The composition according to claim 1, wherein the strain of adherent lactic acid bacteria is able to maintain viability following 1 hour at pH 2.5.

4. The composition according to claim 1, wherein the lactic acid bacterial strain has a 16s-23s spacer region DNA sequence selected from SEQ. ID NO. 1, SEQ. ID NO. 2, or SEQ. ID NO. 3.

5. The composition according to claim 1, wherein the companion animal is a cat.

6. The composition according to claim 1, wherein said composition is in a form selected from the group consisting of a companion animal food, kibbles, chews, a supplement, a gravy, yoghurt, cheese, dairy produce, capsules, tablets, pills, and combinations thereof.

7. The composition according to claim 6, wherein the companion animal food is a cat food.

8. The composition according to claim 6, wherein the companion animal food is selected from the group consisting of a wet animal food and a dry animal food.

9. A method of maintaining or improving the health of a companion animal comprising orally administering a composition comprising a biologically purified strain of adherent lactic acid bacteria of the genus *Lactobacilli* isolated from resected and washed feline gastrointestinal tract having probiotic activity, and having the ability to survive and colonize the gastrointestinal tract of a companion animal, wherein said strain is selected from the group consisting of *Lactobacillus salivarius* ss *salicinius* NCIMB 41287 (AHF 122A), *Lactobacillus animalis* NCIMB 41288 (AHF 223C), and *Lactobacillus reuteri* NCIMB 41289 (AHF 5119) and a carrier.

10. The method according to claim 9, wherein the strain has at least 33% growth when cultured in the presence of 0.5% feline bile salts.

11. The method according to claim 9, wherein the strain is able to maintain viability following 1 hour at pH 2.5.

12. The method according to claim 9, wherein the lactic acid bacterial strain has a 16s-23s spacer region DNA sequence having greater than 94% homology to SEQ. ID NO. 1, greater than 93% homology to SEQ. ID NO. 2, or greater than 98% homology to SEQ. ID NO. 3.

13. The method according to claim 9, wherein the lactic acid bacterial strain has a 16s-23s spacer region DNA sequence selected from SEQ. ID NO. 1, SEQ. ID NO. 2, or SEQ. ID NO. 3.

14. The method according to claim 9, for the regulation of or improvement of the immune system of a companion animal.

15. The method according to claim 14, for treating autoimmune disease in a companion animal.

16. The method according to claim 14, for treating inflammation in a companion animal.

17. The method according to claim 9, for maintaining or improving the health of the skin and/or coat system of a companion animal.

18. The method according to claim 17, for treating atopic disease of the skin of a companion animal.

19. The method according to claim 9, for ameliorating or reducing the effects of aging in a companion animal.

20. The method according to claim 9, for treating weight loss during and following infection in a companion animal.

21. The method according to claim 9, for treating gastrointestinal infection in a companion animal.

22. The method according to claim 21, for improving microbial ecology of a companion animal.

23. The method according to claim 22, comprising reducing the levels of pathogenic bacteria in the faeces of a companion animal.

24. The method according to claim 23, wherein said pathogenic bacteria are selected from the group consisting of *Clostridia, Escherichia, Salmonella*, and mixtures thereof.

25. The method according to claim 9, for treating an urinary tract ailment in a companion animal.

26. The method according to claim 25, wherein said urinary tract ailment comprises urinary tract infection.

27. The method according to claim 25, wherein said urinary tract ailment comprises urinary tract stones.

28. The method according to claim 9, for increasing fiber digestion in a companion animal.

29. The method according to claim 9, for reducing stress levels in a companion animal.

30. The method according to claim 29, wherein said stress levels are measured by determining the level of stress hormones selected from the group consisting of epinephrine, norepinephrine, dopamine, cortisol, C-reactive protein and mixtures thereof.

31. The method according to claim 9, wherein the strain is fed to a companion animal in any amount from 1.0E+04 to 1.0E+12 CFU/animal per day.

32. The method according to claim 9, wherein the companion animal is a cat.

33. A method of reducing odor associated with the feces or urine of a companion animal comprising orally administering a composition comprising a biologically purified strain of adherent lactic acid bacteria of the genus *Lactobacilli* isolated from resected and washed feline gastrointestinal tract, having probiotic activity, and having the ability to survive and colonize the gastrointestinal tract of a companion animal, wherein said strain is selected from the group consisting of *Lactobacillus salivarius* ss *salicinius* NCIMB 41287 (AHF 122A), *Lactobacillus animalis* NCIMB 41288 (AHF 223C), and *Lactobacillus reuteri* NCIMB 41289 (AHF 5119), and a carrier.

34. A method of reducing odor associated with a litter box of a companion animal comprising orally administering a composition comprising a biologically purified strain of adherent lactic acid bacteria of the genus *Lactobacilli* isolated from resected and washed feline gastrointestinal tract, having probiotic activity, and having the ability to survive and colonize the gastrointestinal tract of a companion animal, wherein said strain is selected from the group consisting of *Lactobacillus salivarius* ss *salicinius* NCIMB 41287 (AHF 122A), *Lactobacillus animalis* NCIMB 41288 (AHF 223C), and *Lactobacillus reuteri* NCIMB 41289 (AHF 5119), and a carrier.

35. The method according to claim 34, wherein said composition is in a form selected from the group consisting of a companion animal food, kibbles, chews, a supplement, a gravy, yoghurt, cheese, dairy produce, capsules, tablets, pills, and combinations thereof.

* * * * *